(12) United States Patent
Asano et al.

(10) Patent No.: US 11,813,733 B2
(45) Date of Patent: Nov. 14, 2023

(54) MEDICAL ROBOT SYSTEM, DATA ANALYSIS APPARATUS, AND MEDICAL-ROBOT MONITORING METHOD

(71) Applicants: SYSMEX CORPORATION, Kobe (JP); Medicaroid Corporation, Kobe (JP)

(72) Inventors: Kaoru Asano, Kobe (JP); Yasuhiro Kouchi, Kobe (JP); Mitsuichi Hiratsuka, Kobe (JP); Tetsuya Nakanishi, Kobe (JP)

(73) Assignees: SYSMEX CORPORATION, Kobe (JP); MEDICAROID CORPORATION, Kobe (JP)

( * ) Notice: Subject to any disclaimer, the term of this patent is extended or adjusted under 35 U.S.C. 154(b) by 143 days.

(21) Appl. No.: 16/707,210

(22) Filed: Dec. 9, 2019

(65) Prior Publication Data

US 2020/0114511 A1 Apr. 16, 2020

Related U.S. Application Data

(63) Continuation of application No. 15/373,525, filed on Dec. 9, 2016, now Pat. No. 10,500,728.

(30) Foreign Application Priority Data

Dec. 11, 2015 (JP) ................................ 2015-242730

(51) Int. Cl.
*B25J 9/16* (2006.01)
*A61B 34/30* (2016.01)
(Continued)

(52) U.S. Cl.
CPC ............. *B25J 9/1674* (2013.01); *A61B 34/30* (2016.02); *B25J 9/1689* (2013.01); *A61B 34/35* (2016.02);
(Continued)

(58) Field of Classification Search
CPC ....... B25J 9/1674; B25J 9/1689; A61B 34/30; A61B 2034/2065; A61B 2090/0818;
(Continued)

(56) References Cited

U.S. PATENT DOCUMENTS

2003/0061857 A1* 4/2003 Keller .................... G01W 1/18
73/1.01
2005/0149001 A1 7/2005 Uchikubo et al.
(Continued)

FOREIGN PATENT DOCUMENTS

CN 102036789 A 4/2011
CN 104582912 A 4/2015
(Continued)

OTHER PUBLICATIONS

The Office Action dated Apr. 27, 2020 in a counterpart Chinese patent application.
(Continued)

*Primary Examiner* — Jason Holloway
(74) *Attorney, Agent, or Firm* — METROLEX IP LAW GROUP, PLLC

(57) ABSTRACT

Disclosed is a medical robot system including medical robots placed at different locations and a data analysis apparatus. Each of the medical robots includes a controller that transmits data on a state of operation of the medical robot to the data analysis apparatus. The data analysis apparatus includes a data analysis unit that generates a reference for determining whether or not the medical robots are normal, based on the data transmitted from the medical robots. The data analysis unit monitors the data transmitted from each of the medical robots in operation based on the reference.

17 Claims, 17 Drawing Sheets

(51) Int. Cl.
  *A61B 34/35* (2016.01)
  *A61B 34/20* (2016.01)
  *A61B 90/00* (2016.01)

(52) U.S. Cl.
  CPC ............ *A61B 2034/2059* (2016.02); *A61B 2034/2065* (2016.02); *A61B 2090/0818* (2016.02); *G05B 2219/31334* (2013.01); *G05B 2219/45117* (2013.01); *Y10S 901/01* (2013.01); *Y10S 901/46* (2013.01)

(58) Field of Classification Search
  CPC ............ A61B 2034/2059; A61B 34/35; G05B 2219/45117; G05B 2219/31334; Y10S 901/46; Y10S 901/01
  See application file for complete search history.

(56) References Cited

U.S. PATENT DOCUMENTS

| | | | |
|---|---|---|---|
| 2006/0206289 A1* | 9/2006 | Stake | G05B 19/4183 702/184 |
| 2007/0287992 A1* | 12/2007 | Diolaiti | A61B 34/37 606/1 |
| 2008/0247549 A1* | 10/2008 | Blanc | B25J 9/1674 380/277 |
| 2011/0028894 A1 | 2/2011 | Foley et al. | |
| 2013/0131845 A1 | 5/2013 | Guilleminot | |
| 2014/0005684 A1 | 1/2014 | Kim et al. | |
| 2014/0309659 A1 | 10/2014 | Roh et al. | |
| 2014/0320392 A1 | 10/2014 | Chizeck et al. | |
| 2014/0324070 A1* | 10/2014 | Min | A61B 34/30 606/130 |
| 2014/0365235 A1 | 12/2014 | DeBoer et al. | |
| 2015/0100066 A1 | 4/2015 | Kostrzewski et al. | |
| 2015/0150637 A1 | 6/2015 | Iwasa | |
| 2016/0149996 A1* | 5/2016 | Eckert | H04L 67/2842 709/217 |

FOREIGN PATENT DOCUMENTS

| | | |
|---|---|---|
| EP | 1958738 A1 | 8/2008 |
| EP | 2942029 A1 | 11/2015 |
| JP | 2001265432 A | 9/2001 |
| JP | 2002092183 A | 3/2002 |
| JP | 2002272758 A | 9/2002 |
| JP | 2005-087421 A | 4/2005 |
| JP | 2005111085 A | 4/2005 |
| JP | 2005-148873 A | 6/2005 |
| JP | 2011-204205 A | 10/2011 |
| JP | 2012061195 A | 3/2012 |
| JP | 3185040 U | 8/2013 |
| JP | 2014000117 A | 1/2014 |
| JP | 2014042660 A | 3/2014 |
| JP | 2015527906 A | 9/2015 |
| KR | 20100112310 A | 10/2010 |
| WO | 2015129395 A1 | 9/2015 |
| WO | 2015142933 A1 | 9/2015 |
| WO | 2016187002 A1 | 11/2016 |

OTHER PUBLICATIONS

The Office Action dated Jul. 14, 2020 in a counterpart Japanese patent application.
The Office Action dated Feb. 18, 2021 in a counterpart Chinese patent application.
The Japanese Office Action (JPOA) dated Oct. 5, 2021, in a related Japanese patent application.
The extended European search report (EESR) dated Mar. 14, 2022 in a counterpart European patent application.
The Japanese Office Action (JPOA) dated Jun. 6, 2023 in a related Japanese patent application.
The Japanese Office Action (JPOA) dated Mar. 28, 2023, in a related Japanese patent application.
The Japanese Office Action (JPOA) dated Aug. 16, 2023 in a related Japanese patent application.

* cited by examiner

FIG. 15A

| SYSTEM ID (220) | COMPONENT ID (221) | MONITORING-TARGET DATA (222) | TIMESTAMP (223) |
|---|---|---|---|

| SYSTEM ID (220) | COMPONENT ID (221) | DATA ID (224) | MONITORING-TARGET DATA (222) | TIMESTAMP (223) |
|---|---|---|---|---|

| SYSTEM ID (220) | INDIVIDUAL IDENTIFICATION INFORMATION OF ARM (230) | MODEL NUMBER INFORMATION OF ARM (231) | USAGE COUNT (232) | ATTACHMENT PORT ID (233) |
|---|---|---|---|---|

(213)

MEDICAL ROBOT SYSTEM, DATA ANALYSIS APPARATUS, AND MEDICAL-ROBOT MONITORING METHOD

CROSS REFERENCE TO RELATED APPLICATION

This application is a continuation of application Ser. No. 15/373,525, filed on Dec. 9, 2016, which is based upon and claims the benefit of priority from the prior Japanese Patent Application No. 2015-242730, filed on Dec. 11, 2015, the entire contents of all of which are incorporated herein by reference.

BACKGROUND

The disclosure relates to a robot for use in surgeries.

In recent years, there have been more and more cases where surgery is performed using a surgery assistance robot, and there have been increasing needs to provide more elaborated support (hereinafter, referred to as "support") for such a surgery assistance robot.

Related Art 1 to 3 relate to supporting a surgery assistance robot.

Related Art 1 discloses a technique in which setting information on equipment being used in an operating room is transmitted to a support room provided at a location remote from the operating room. The support room monitors whether or not the setting information received is within an appropriate range, and notifies warning information to the operating room when the setting information is not within the appropriate range (see Patent Literature 1).

Related Art 2 discloses a remote surgery assistance system that relates to an apparatus to be used in an operating room and performs an operation check before a surgery. This system performs an operation check before a surgery, and performs a remote repair or sends a support person (see Patent Literature 2).

Related Art 3 discloses a technique in which the torque value of a drive motor in operation of a robotic arm is saved at a predetermined interval, and an abnormality is detected from the value of the torque fluctuation (see Patent Literature 3).

Patent Literature 1: Japanese Patent Application Publication No. 2005-111080
Patent Literature 2: Japanese Patent Application Publication No. 2007-7040
Patent Literature 3: Japanese Patent Application Publication No. 2006-281421

SUMMARY

One or more embodiments of a medical robot system may comprise medical robots placed at different locations and a data analysis apparatus, in which each of the medical robots includes a controller that transmits data on a state of operation of the medical robot to the data analysis apparatus, the data analysis apparatus includes a data analysis unit that generates a reference for determining whether or not the medical robots are normal, based on the data transmitted from the medical robots, and the data analysis unit monitors the data transmitted from each of the medical robots in operation based on the reference.

One or more embodiments of a data analysis apparatus capable of communicating with medical robots placed in different operating rooms may comprise: a database that stores data on a state of operation of each of the medical robots; and a data analysis unit that generates a reference for determining whether or not the medical robots are normal, based on the data transmitted from the medical robots, in which the data analysis unit monitors the data transmitted from each of the medical robots in operation based on the reference.

One or more embodiments of a medical-robot monitoring method may comprise causing a data analysis apparatus to receive data on a state of operation of each of medical robots placed in different operating rooms; generating a reference for determining whether or not the medical robots are normal, based on the data transmitted from the medical robots; and monitoring the data transmitted from each of the medical robots in operation based on the reference.

BRIEF DESCRIPTION OF DRAWINGS

FIG. 15A and FIG. 15B are diagrams illustrating data structures in a database according to an embodiment.

FIG. 16 is a diagram illustrating a data structure in the database according to an embodiment.

EMBODIMENTS

An embodiment is described below with reference to the drawings. In this embodiment, surgery systems 100 including surgical operation robots are exemplarily described.

[System Configuration]

Figure 1:
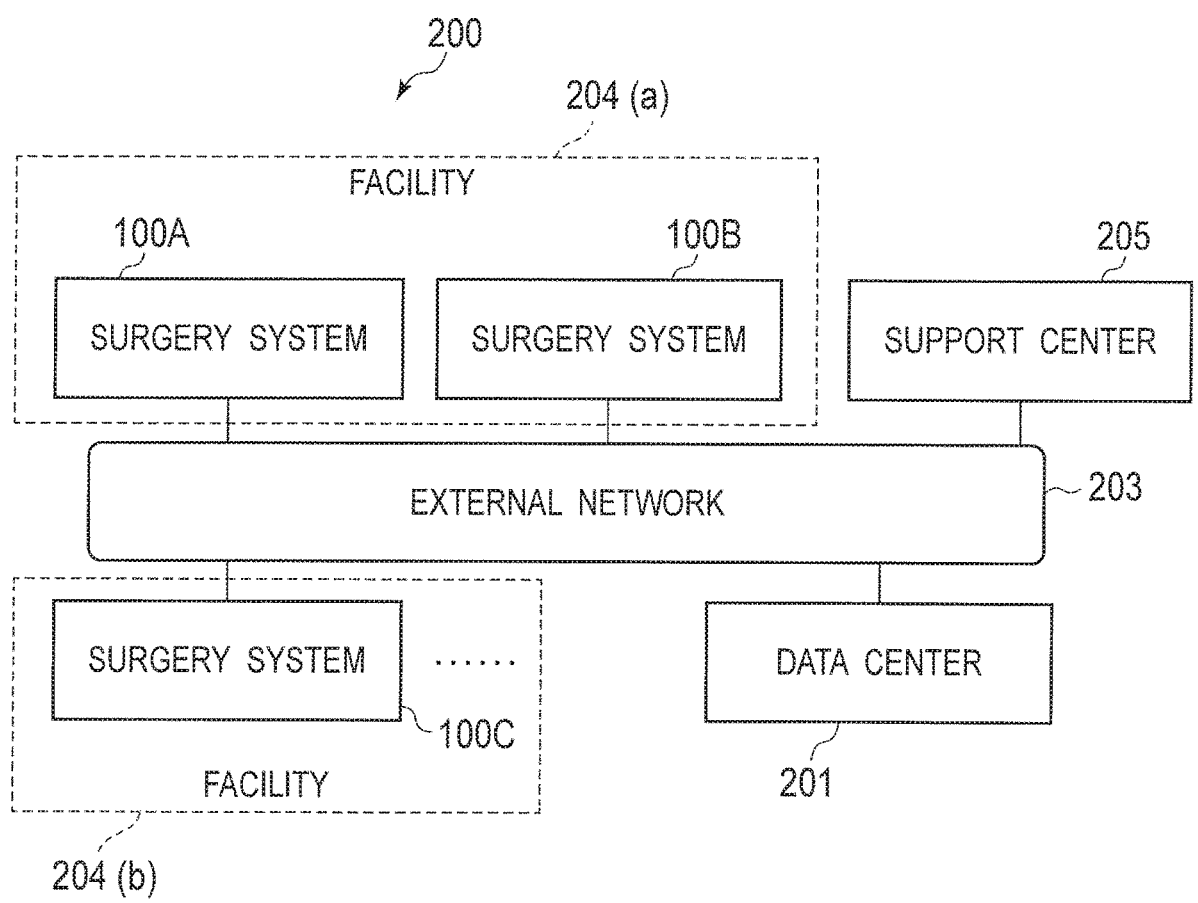
FIG. 1 illustrates a configuration diagram of a system according to an embodiment.

FIG. 1 illustrates an example of a system configuration in this embodiment. In system 200 in FIG. 1, surgery systems 100 and data center 201 (including a data analysis apparatus in this embodiment) are connected to each other (capable of communicating with each other) via external network 203 provided outside facilities 204 such as research institutions or medical institutions. Data center 201 performs centralized control of surgery systems 100. External network 203 is the Internet, for example. Each surgery system 100 transmits and receives data on the state of operation of surgery system 100 to and from data center 201 via external network 203. Data center 201 can communicate with support center 205 via external network 203.

Figure 2:
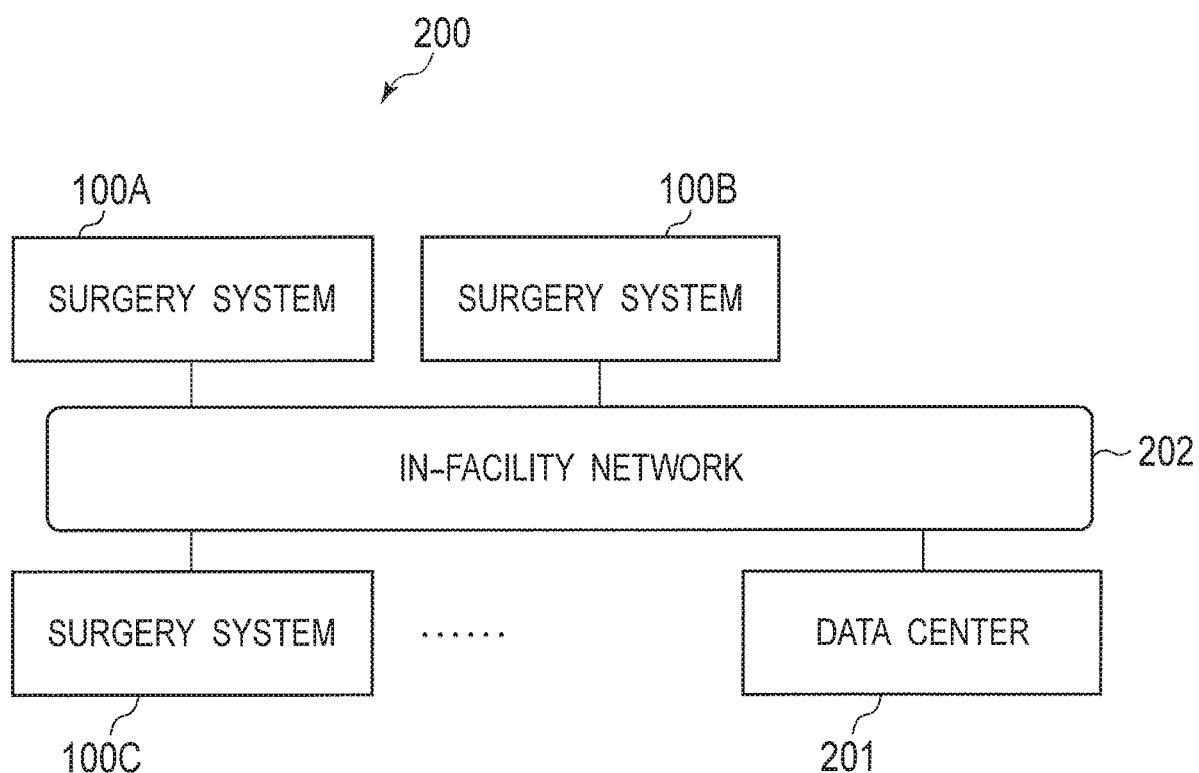
FIG. 2 illustrates a configuration diagram of a system according to an embodiment.

FIG. 2 illustrates a system configuration in this embodiment. In system 200, surgery systems 100 and data center 201 (including a data analysis apparatus in this embodiment) are connected to each other (capable of communicating with each other) via a network. FIG. 2 illustrates a system in which surgery systems 100 and data center 201 are connected to each other via in-facility network 202 provided inside a facility such as a research institution or a medical institution. Data center 201 performs centralized control of surgery systems 100 inside the facility. Each surgery system 100 transmits and receives data on the state of operation of surgery system 100 to and from data center 201 via in-facility network 202. Details of surgery system 100 are described later.

In the examples of FIG. 1 and FIG. 2, each surgery system 100 and data center 201 each have unique identification information. When each surgery system 100 and data center 201 communicate with each other, the identification information of each is used as information indicating the address to which or from which data is transmitted.

In the examples of FIG. 1 and FIG. 2, surgery systems 100 are installed in different operating rooms.

[Brief Description of Surgery System]

Figure 3:
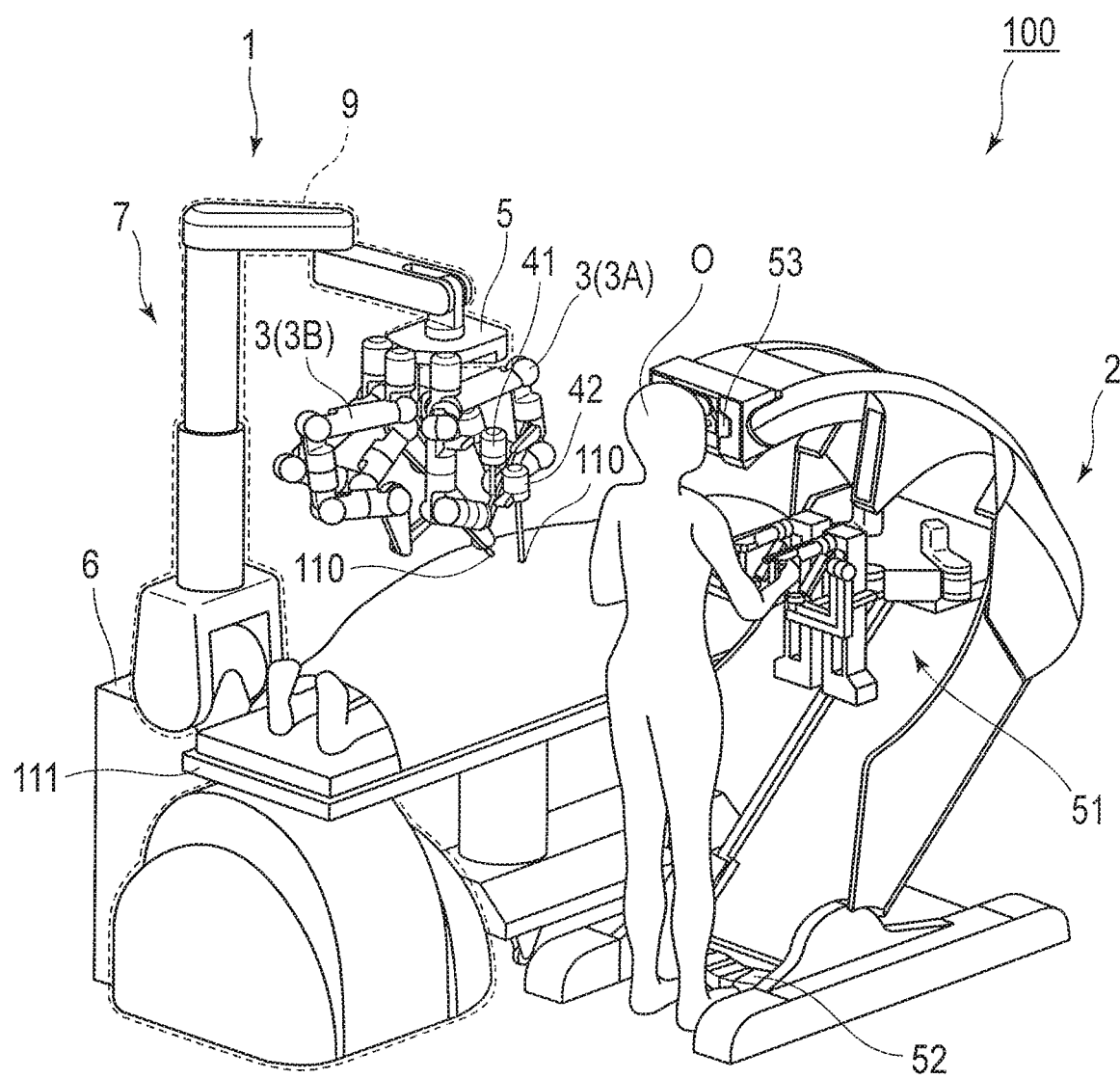
FIG. 3 illustrates a schematic view illustrating the configuration of a surgery system according to an embodiment.

FIG. 3 is a schematic view illustrating the entire configuration of surgery system 100 according to an embodiment. As illustrated in FIG. 3, surgery system 100 is a system with which operator O such as a doctor performs an endoscopic surgery on patient P by using patient-side system 1, as in a robot-assisted surgery or a robotic telesurgery.

Surgery system 100 includes patient-side system 1 and manipulation apparatus 2 with which to manipulate this patient-side system 1. Manipulation apparatus 2 is placed away from patient-side system 1, and patient-side system 1 is remotely manipulated by manipulation apparatus 2. Operator O inputs a motion to be made by patient-side system 1 into manipulation apparatus 2, and manipulation apparatus 2 transmits that motion command to patient-side system 1. Then, patient-side system 1 receives the motion command transmitted from manipulation apparatus 2 and actuates endoscope assembly 41, instrument 42, or the like provided to patient-side system 1 based on the motion command. Constituent elements of surgery system 100 are described below in detail. In the following description, patient-side system 1 and manipulation apparatus 2 in surgery system 100 are collectively referred to as "surgery robot".

[Example Configuration of Manipulation Apparatus]

Manipulation apparatus 2 is an apparatus which provides an interface between surgery system 100 and operator O and with which to manipulate patient-side system 1. Manipulation apparatus 2 is installed in an operating room by operating table 111 or at a distance from operating table 111, or is installed outside the operating room. Manipulation apparatus 2 includes action input unit 50 such as manipulator arm 51 and manipulation pedal 52 for manipulation with which operator O inputs motion commands, and monitor 53 that displays images captured by endoscope assembly 41. Visually checking the affected area on monitor 53, operator O manipulates action input unit 50 to input motion commands into manipulation apparatus 2. The motion commands inputted into manipulation apparatus 2 are transmitted wiredly or wirelessly to later-described controller 6 of patient-side system 1.

[Example Configuration of Patient-Side System]

Patient-side system 1 provides an interface between surgery system 100 and patient P. Patient-side system 1 is installed in the operating room by operating table 111, on which patient P lies. The inside of the operating room is sterilized and is thus a sterile field.

Patient-side system 1 includes: positioner 7; platform 5 attached at a tip portion of positioner 7; patient-side manipulator arms (hereinafter, simply referred to as "arms 3" (movable parts)) detachably attached to platform 5; endoscope assembly 41, attached to a tip portion of one arm 3A among arms 3; instruments 42, detachably attached to tip portions of other arms 3B among arms 3; sterile drape 9 screening positioner 7 and platform 5 from the sterile field; and controller 6 controls the motion of patient-side system 1. In the following, arm 3 to which endoscope assembly 41 is attached is also referred to as "camera arm 3A", and arms 3 to which instruments 42 are attached are also referred to as "instrument arms 3B". Patient-side system 1 according to this embodiment includes four arms 3 in total, including one camera arm 3A and three instrument arms 3B.

In above-mentioned patient-side system 1, the elements from positioner 7 to endoscope assembly 41 and to each instrument 42 are connected in series. In this description, an end portion within the above-mentioned series of components closer to positioner 7 (more specifically, closer to the portion of positioner 7 in contact with the floor of the operating room) is referred to as "base end portion", whereas the opposite end portion is referred to as "tip portion". Moreover, the base end portion is also referred to as "proximal end portion", and the tip portion is also referred to as "distal end portion".

Figure 8:
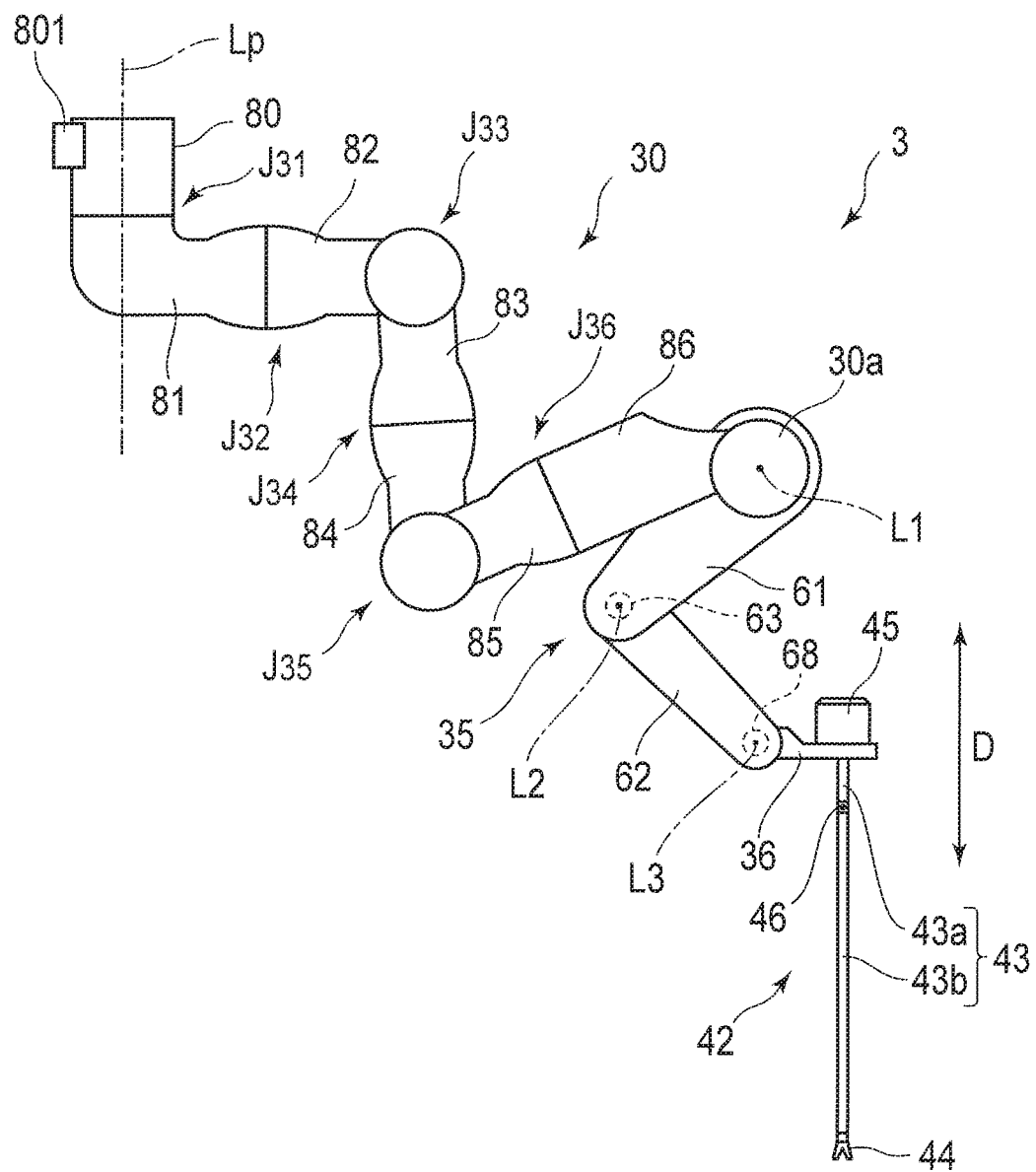
FIG. 8 is a schematic view illustrating the entire configuration of an arm entire.

Each instrument 42 includes drive unit 45 provided at its base end portion, end effector 44 provided at its tip portion, and long and narrow shaft 43 connecting drive unit 45 and end effector 44 (see FIG. 8 for these components). Reference direction D is defined for instrument 42, and drive unit 45, shaft 43, and end effector 44 are arranged in parallel to reference direction D. End effector 44 of instrument 42 is selected from a group of tools including articulated tools capable of their own motions (e.g. forceps, scissors, grasper, needle holder, micro dissector, staple applier, tacker, aspiration-cleaning tool, snare wire, clip applier, etc.) and unarticulated tools (e.g. a cutting blade, cautery probe, cleaning tool, catheter, aspiration orifice, etc).

In patient-side system. 1 with the above-described configuration, upon receipt of motion commands from manipulation apparatus 2, controller 6 firstly positions platform 5 by actuating positioner 7 such that platform 5 and operating table 111 or patient P have a predetermined positional relation with each other. Controller 6 then positions endoscope assembly 41 and instruments 42 by actuating arms 3 such that sleeves (cannula sleeves) 110 held on the body of patient P, endoscope assembly 41 and instruments 42 have predetermined initial positional relations with each other. Note that positioner 7 and arms 3 may be actuated at the same time for the positioning. With positioner 7 held still as a rule, controller 6 then performs surgery by actuating instruments 42 while actuating arms 3 to change the positions and postures of endoscope assembly 41 and instruments 42 as appropriate in accordance with the motion commands from manipulation apparatus 2.

[Example Configuration of Positioner]

Figure 4:
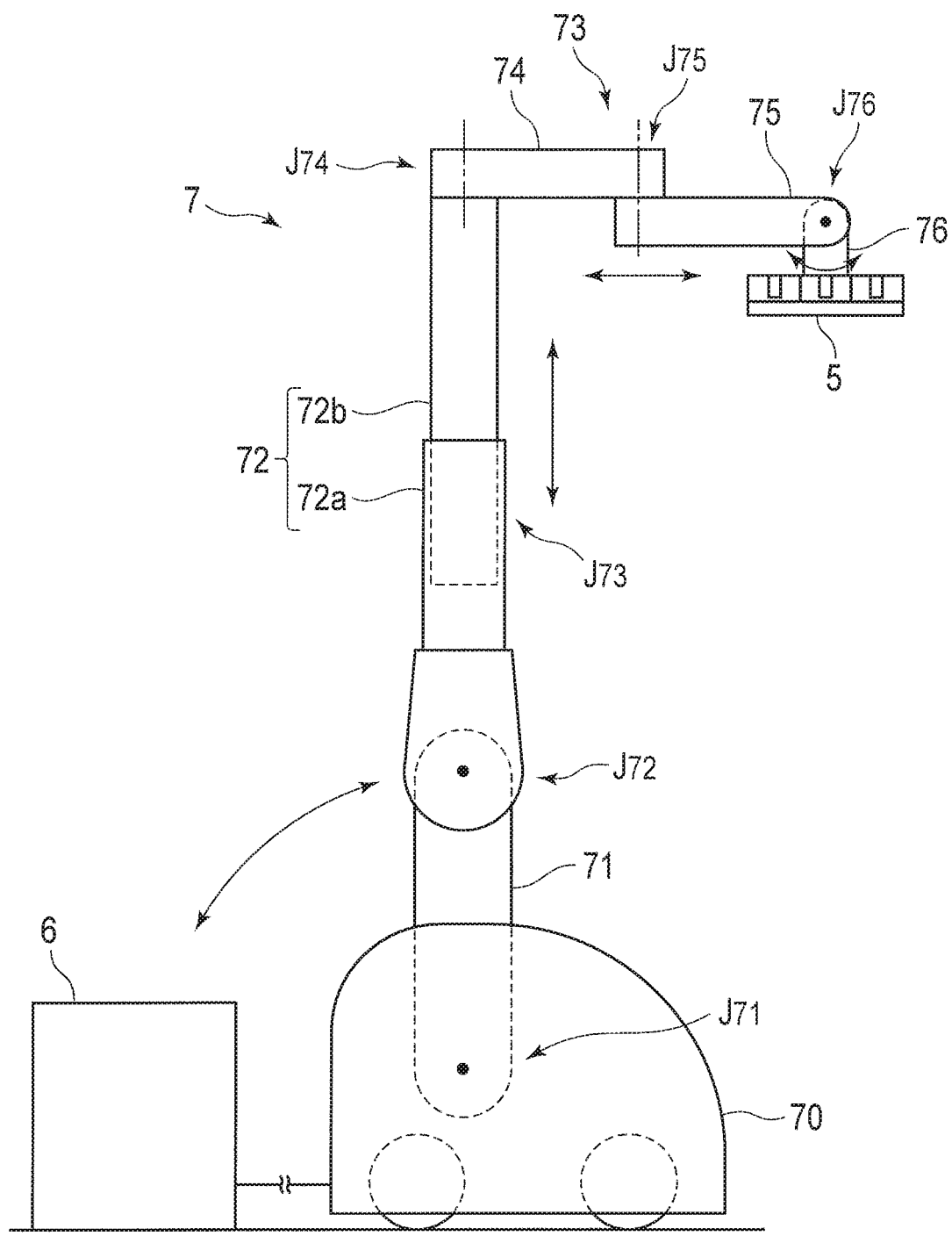
FIG. 4 is a side view illustrating the entire configuration of a positioner.

Now, the configuration of positioner 7 is described in detail. FIG. 4 is a side view illustrating the entire configuration of positioner 7.

As illustrated in FIG. 4, positioner 7 is basically designed as a horizontal articulated robot, and includes base 70 placed on the floor of the operating room, hoist shaft 72, swingarm 71 coupling base 70 and a base end portion of hoist shaft 72, and horizontal arm 73 coupled to a tip portion of hoist shaft 72. Platform. 5 is coupled to a tip portion of horizontal arm 73.

Base 70 is, for example, a carriage with a brake and can be moved to and stopped at a desired position. A base end portion of swingarm 71 is coupled to this base 70 via rotary joint J71. With the motion of this rotary joint J71, swingarm 71 turns (swings) about a horizontal rotation axis (swing axis) defined in base 70. Also, a tip portion of swingarm 71 is coupled to the base end portion of hoist shaft 72 via rotary joint J72. With the motion of this rotary joint J72, swingarm 71 turns (swings) about a horizontal rotation axis defined at the base end portion of hoist shaft 72.

Hoist shaft 72 extends vertically and is vertically extendable and retractable. Hoist shaft 72 in this embodiment includes tubular member 72a, hollow shaft member 72b inserted in this tubular member 72a such that it can move vertically inward and outward, and translational joint J73 coupling tubular member 72a and shaft member 72b. With the motion of this translational joint J73, shaft member 72b moves vertically inward and outward relative to tubular member 72a.

Horizontal arm 73 includes first link 74 and second link 75 extending horizontally and wrist link 76 coupled to a tip portion of second link 75. Platform 5 is connected to a tip portion of wrist link 76.

Abase end portion of first link 74 is coupled to the tip portion of hoist shaft 72 via rotary joint J74. First link 74 and hoist shaft 72 are at a right angle to each other. With the motion of above-mentioned rotary joint J74, first link 74 turns about a vertical rotation axis defined at the tip portion of hoist shaft 72. A tip portion of first link 74 is coupled to a base end portion of second link 75 via rotary joint J75. With the motion of this rotary joint J75, second link 75 turns about a vertical rotation axis defined at the tip portion of first link 74.

The tip portion of second link 75 is coupled to abase end portion of wrist link 76 via rotary joint J76. With the motion of this rotary joint J76, wrist link 76 turns about a horizontal rotation axis defined at the tip portion of second link 75. Wrist link 76 in a normal state extends vertically, and platform 5 connected to the tip portion of this wrist link 76 is in a horizontal posture.

Figure 5:
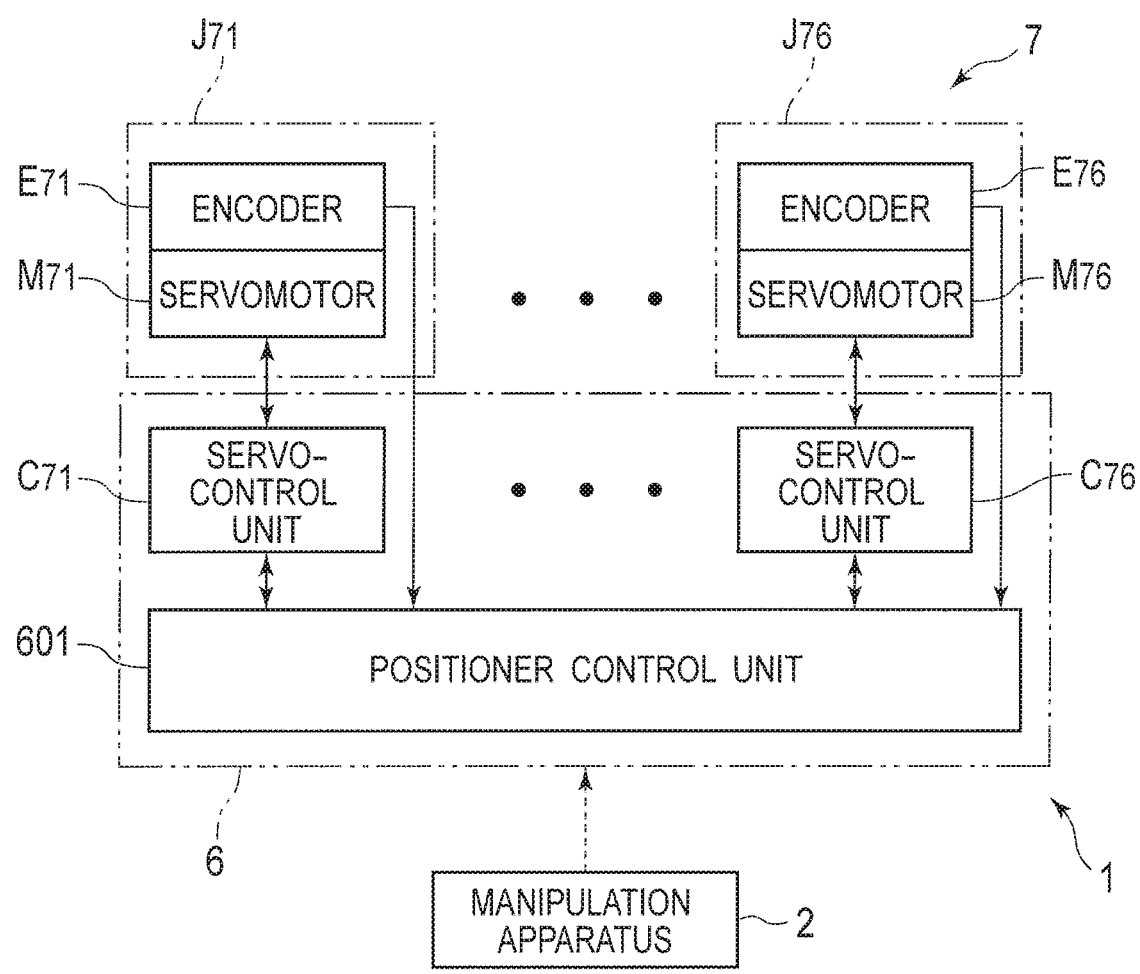
FIG. 5 is a block diagram illustrating a schematic configuration of control systems for the positioner.

Now, the configuration of control systems for positioner 7 is described. FIG. 5 is a block diagram illustrating a schematic configuration of the control systems for positioner 7. As illustrated in FIG. 5, for joints J71 to J76, positioner 7 includes servomotors M71 to M76 for driving and encoders E71 to E76 that detects the rotational angles of servomotors M71 to M76, respectively. Servomotors M71 to M76 are each provided with a temperature sensor. Note that in this figure, among the drive systems for joints J71 to J76, the drive systems for rotary joint J71 and rotary joint J76 are representatively illustrated, and illustration of the drive systems for other joints J73 to J75 is omitted.

Controller 6 includes positioner control unit 601 that controls the motion of positioner 7. Servo-control units C71 to C76 are electrically connected to positioner control unit 601, and servomotors M71 to M76 are electrically connected to servo-control units C71 to C76 via amplification circuits and the like not illustrated. Controller 6 can communicate with data center 201 via in-facility network 202 or external network 203.

In the above-described configuration, a position-posture command for platform 5 is inputted into positioner control unit 601 based on a motion command inputted into manipulation apparatus 2. Positioner control unit 601 generates position command values based on the position-posture command and the rotational angles detected by encoders E71 to E76, and outputs them. Acquiring these position command values, servo-control units C71 to C76 generate drive command values (torque command values) based on the rotational angles detected by encoders E71 to E76 and the position command values, and output them. Acquiring these drive command values, the amplification circuits feed drive currents corresponding to the drive command values to servomotors M71 to M76. Thus, servomotors M71 to M76 are servo-controlled such that platform 5 reaches the position and the posture corresponding to the position-posture command.

Controller 6 transmits data on components that serves as movable parts of positioner 7 (e.g. joints J71 to J76) to data center 201. Controller 6 transmits the following data, for example, to data center 201 via in-facility network 202 or external network 203.

The position command values outputted to servo-control units C71 to C76

The drive command values (torque command values) outputted from servo-control units C71 to C76

The current values of the drive currents fed from the amplification circuits

The temperatures collected by the temperature sensors disposed at servomotors M71 to M76

The encoder values of encoders E71 to E76 corresponding to the drive currents The voltage values of backup batteries for encoders E71 to E76

The electric resistance values of harnesses provided in joints J71 to J76

Controller 6 can transmit image data on positioner 7 captured by at least one camera (not illustrated) provided to surgery system 100 to data center 201. Controller 6 acquires the image data from the camera and transmits the acquired data to data center 201. The camera can capture a still image of positioner 7, and controller 6 can transmit the captured still image data to data center 201. Also, the camera can capture the motion of positioner 7 in a video, and controller 6 can transmit the captured video data to data center 201.

Controller 6 may also transmit information indicating conditions of the operating room to data center 201.

Controller 6 transmits the above-mentioned information to data center 201 in association with the identification information (component IDs) of the components that serve as the movable parts of positioner 7 (e.g. joints J71 to J76).

The data to be transmitted by controller 6 to data center 201 is not limited to the above-described example. Controller 6 can transmit the above-described data to data center 201 each time a motion command is inputted from manipulation apparatus 2.

As described above, positioner 7 can change its state in accordance with a position-posture command for platform 5. Here, as illustrated in FIG. 4, the basic posture of positioner 7 is a state where swingarm 71 and hoist shaft 72 extend vertically, horizontal arm 73 extends horizontally, and platform 5, connected to wrist link 76, lies horizontally.

Figure 6:
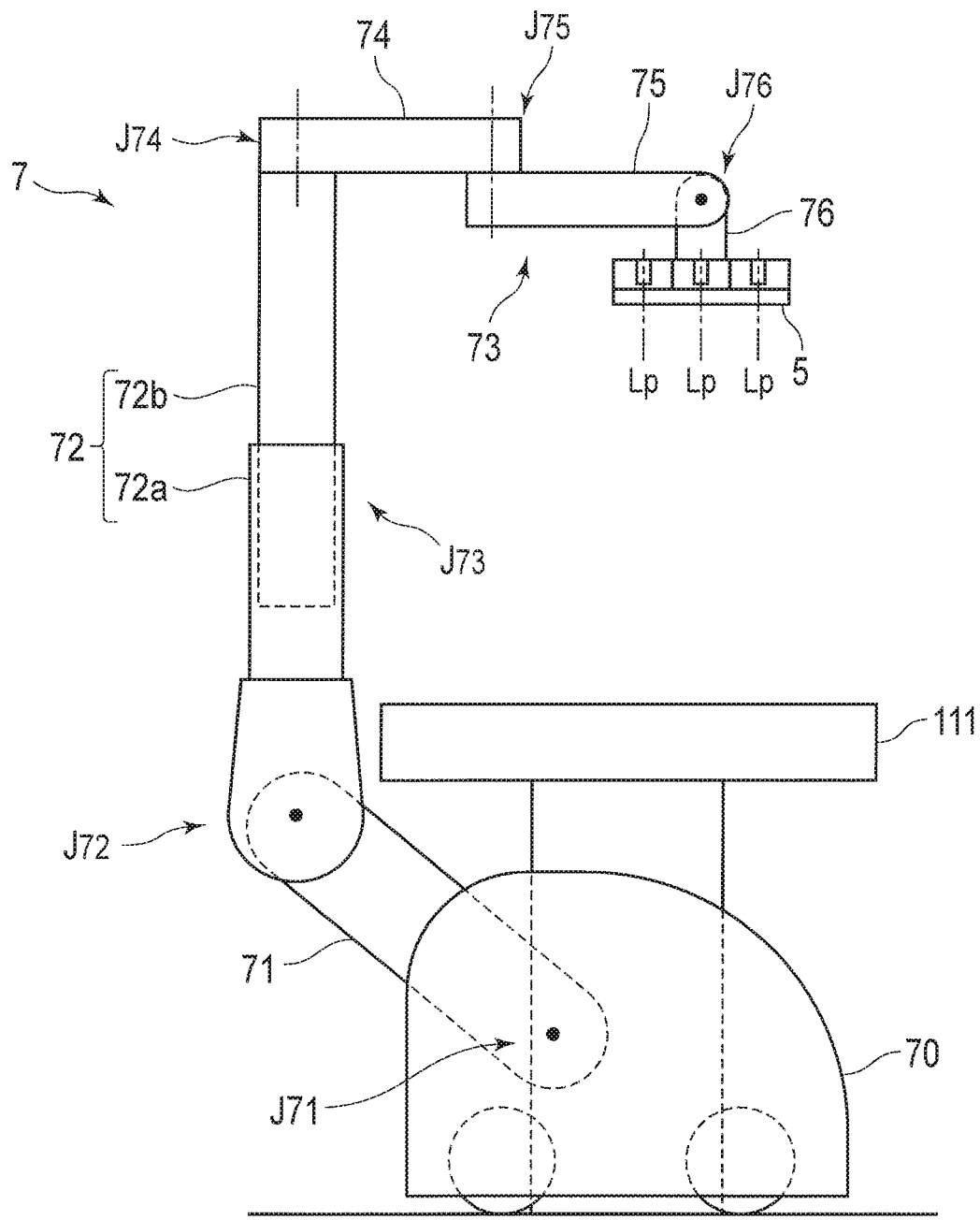
FIG. 6 is a side view illustrating the entire configuration of the positioner with its swingarm tilted from a vertical position.

As illustrated in FIG. 6, when tilting swingarm 71 from its vertical posture in the above-described basic posture, positioner control unit 601 actuates rotary joint J71 to tilt swingarm 71 from the vertical posture and actuates rotary joint J72 to maintain hoist shaft 72 in a vertical posture. In this way, the vertical posture of hoist shaft 72 and the horizontal posture of horizontal arm 73 are maintained even when swingarm 71 is tilted from its vertical posture.

With swingarm 71 tilted from its vertical posture as described above, positioner 7 defines a C-shape as a whole. Thus, positioner 7 can be in a state where base 70 is situated under operating table 111, hoist shaft 72 is situated by the side of operating table 111, and horizontal arm 73 is situated above operating table 111. Keeping base 70 under operating table 111 in this manner leaves sufficient traffic lines during a surgery for assistants who assist the surgery around operating table 111.

Figure 7:
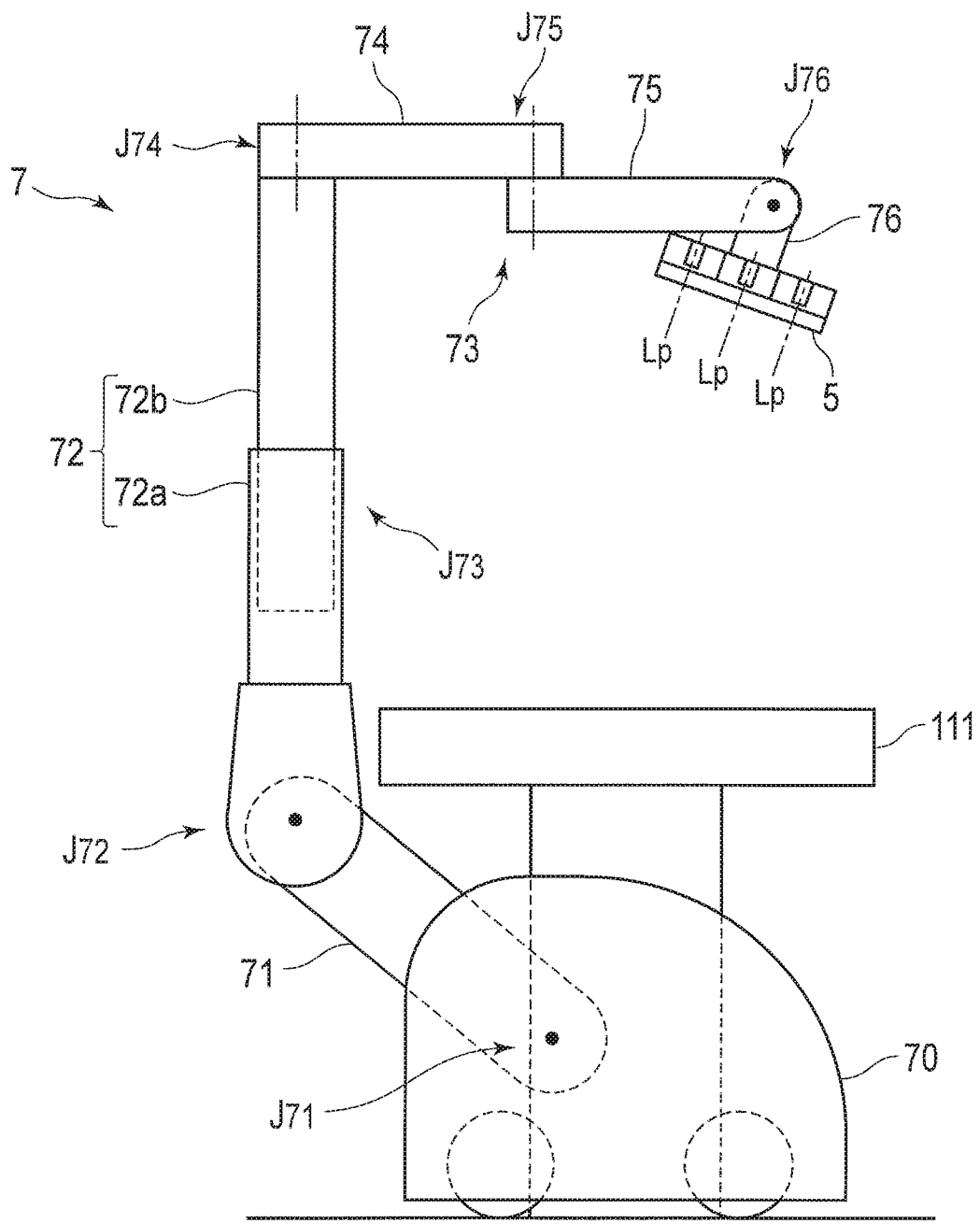
FIG. 7 is a side view illustrating the entire configuration of the positioner with its platform tilted from a horizontal position.

Further, as illustrated in FIG. 7, when rotary joint J76 is driven to tilt wrist link 76 from its vertical posture, platform 5 is tilted from its horizontal posture. When platform 5 is tilted from its horizontal posture, basic axes (turn axes) Lp of arms 3 attached to platform 5 are tilted all at once from their vertical postures. This consequently expands the angular range of reference direction D, defined for each instrument 42, and thus allows instrument 42 to be greatly tilted from its vertical posture and inserted into patient P. Thus, the direction of insertion of instrument 42 into patient P can be appropriately adjusted in accordance with the recumbent position of patient P and the position from which the surgery is performed.

[Example Configuration of Arms]

Now, the configuration of arms 3 is described in detail. FIG. 8 illustrates a schematic configuration of one of arms 3 of patient-side system 1. As illustrated in FIG. 8, arm 3 includes arm body 30 and translational arm 35 coupled to a tip portion of arm body 30, and can move its tip portion relative to its base end portion within a three-directional space. Note that all arms 3 of patient-side system 1 have the same or similar configurations in this embodiment. However, at least one of arms 3 may have a different configuration from the others.

When arm 3 is instrument arm 3B, holder (instrument holder) 36 that holds instrument 42 is provided at the tip of translational arm 35. Instrument 42 is detachably held on holder 36. Shaft 43 of instrument 42 held on holder 36 extends in parallel to reference direction D.

Also, as in above-mentioned instrument arm 3B, when arm 3 is camera arm 3A, holder 36 is provided at a tip portion of translational arm 35, and endoscope assembly 41 is detachably held on this holder 36. Here, holder 36 provided to camera arm 3A may be of a different type from holder 36 provided to instrument arm 3B. Alternatively, endoscope assembly 41 may be fixed to camera arm 3A since endoscope assembly 41 is rarely changed during a surgery.

Arm 3 is freely attachable to and detachable from (that is, easily attached to and detached from) platform 5. Arm 3 has water resistance, heat resistance, and chemical resistance for cleaning and sterilization. There are various methods for the sterilization of arm 3. For example, it is possible to selectively use a method such as high-pressure steam sterilization, EOG sterilization, or chemical sterilization with a disinfectant. In the high-pressure steam sterilization, arm 3 is set inside a closed high-pressure container such as an autoclave and exposed to saturated steam at a predetermined pressure for a predetermined period of time (e.g. at 115° C. for 30 minutes, at 121° C. for 20 minutes, or at 126° C. for 15 minutes). In the EOG sterilization, arm 3 is set inside a closed container, and 450 to 1000 mg/L of ethylene oxide gas is caused to flow inside this container. In the chemical sterilization, arm 3 is immersed in a disinfectant such as glutaral, for example.

[Example Configuration of Arm Body]

Arm body 30 includes base 80 detachably attached to platform 5, and first link 81 to sixth link 86 coupled in this order from base 80 toward the tip. More specifically, a base end portion of first link 81 is coupled to a tip portion of base 80 via torsional joint J31. A base end portion of second link 82 is coupled to a tip portion of first link 81 via torsional joint J32. A base end portion of third link 83 is coupled to a tip portion of second link 82 via bend joint J33. A base end portion of fourth link 84 is coupled to a tip portion of third link 83 via torsional joint J34. A base end portion of fifth link 85 is coupled to a tip portion of fourth link 84 via bend joint J35. A base end portion of sixth link 86 is coupled to a tip portion of fifth link 85 via torsional joint J36. A base end portion of translational arm 35 is coupled to a tip portion of sixth link 86.

The outermost portion of arm body 30 is mainly made of a material that has heat resistance and chemical resistance, such as stainless. Also, a seal (not illustrated) for ensuring water resistance is provided at coupled portions of each pair of links. This seal has heat resistance for high-pressure steam sterilization and chemical resistance against disinfectants. Note that the coupled portions of each pair of links are such that the end portion of one of the coupled links is inserted in the end portion of the other link, and the seal is disposed to fill the gap between the end portions of these links. Thus, the seal is hidden from outside. This prevents ingress of water, chemical solution, and steam from gaps between the seal and the links.

Figure 9:
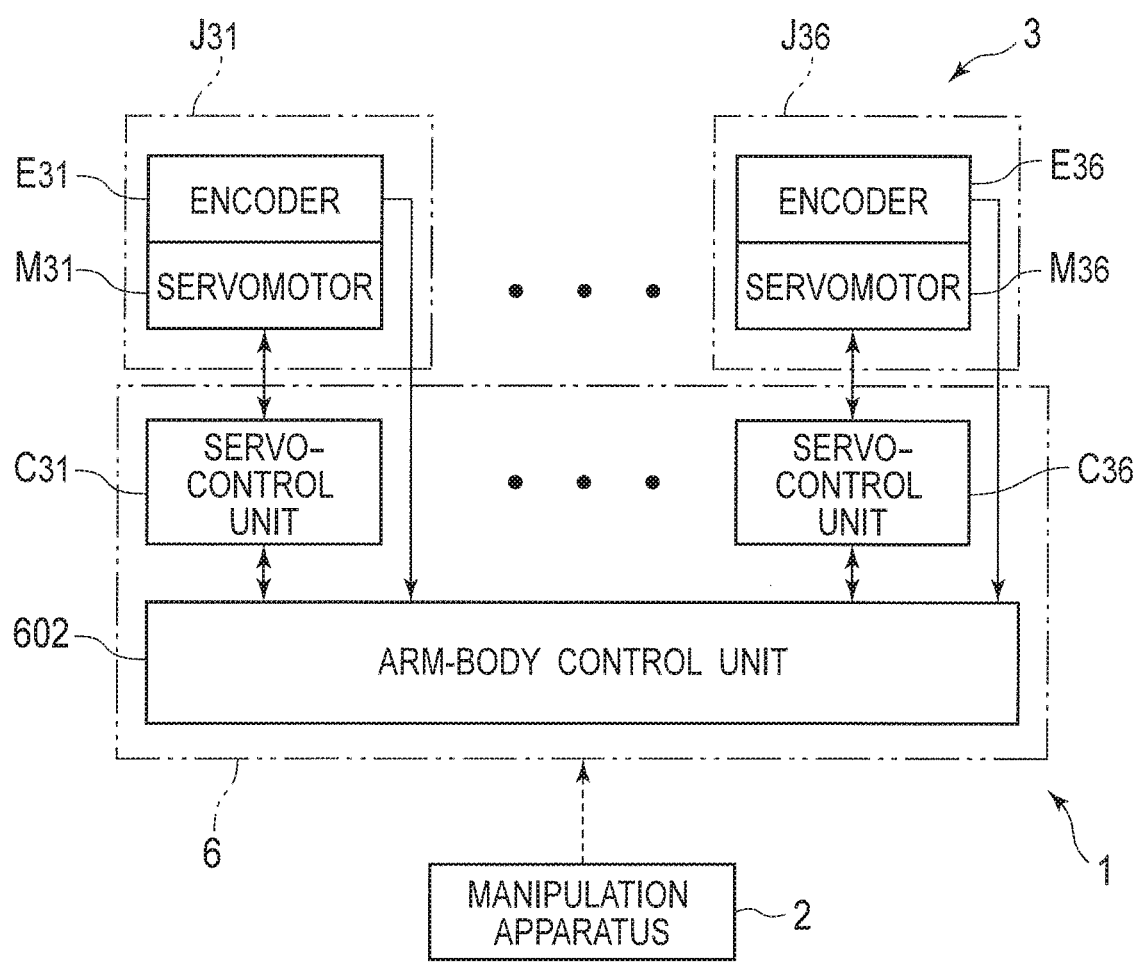
FIG. 9 is a block diagram illustrating a schematic configuration of control systems for an arm body.
Figure 10:
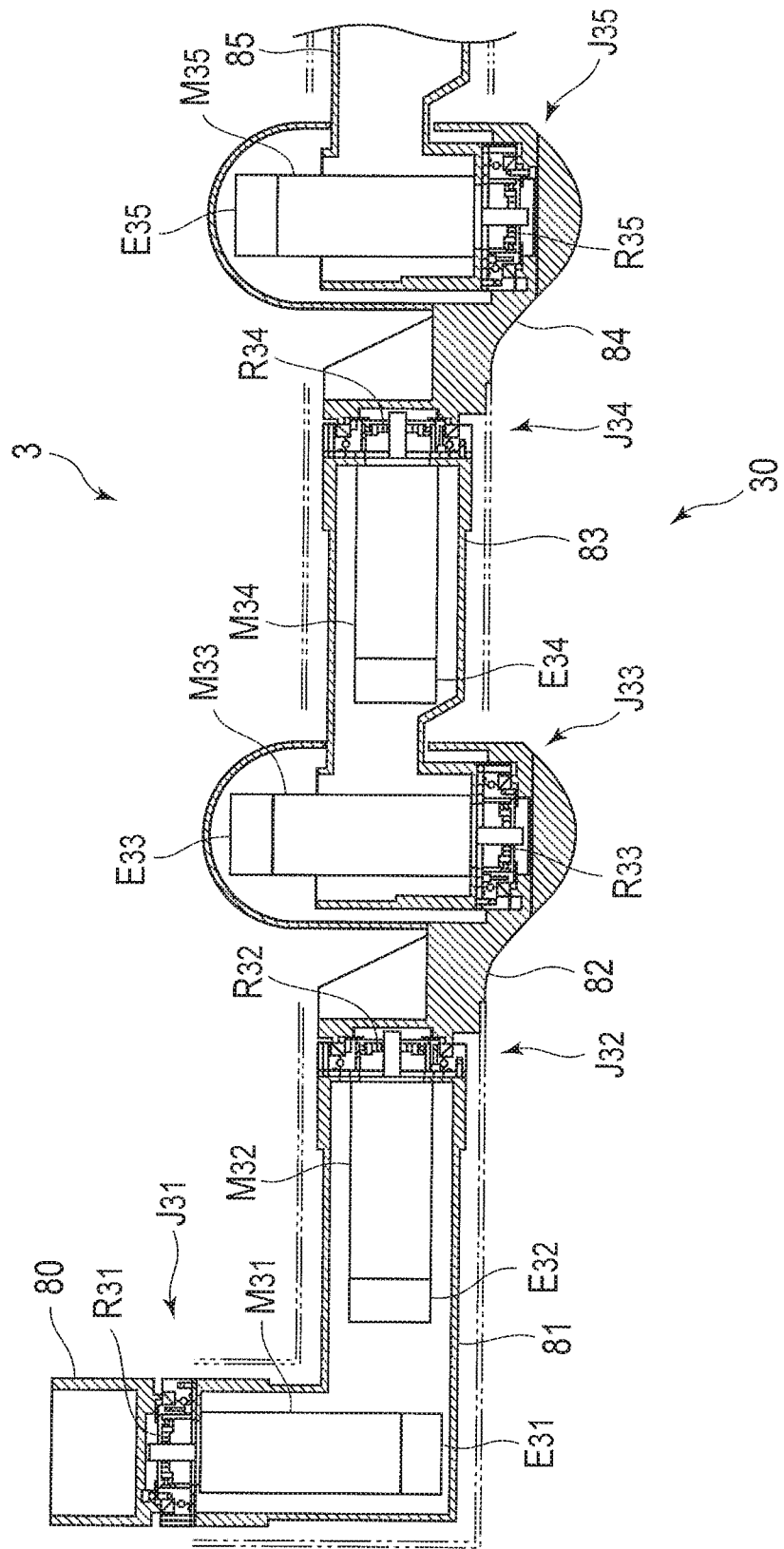
FIG. 10 is a cross-sectional view of part of the arm body illustrating the layout of drive systems for the arm body.

Now, the configurations of drive systems and control systems for arm body 30 are described with reference to FIG. 9 and FIG. 10. FIG. 9 is a block diagram illustrating a schematic configuration of the control systems for arm body 30. FIG. 10 is a schematic cross-sectional view of arm body 30 illustrating the layout of the drive systems for arm body 30.

For joints J31 to J36, arm body 30 with the above-described configuration includes servomotors M31 to M36 for driving, encoders E31 to E36 that detect the rotational angles of servomotors M31 to M36, and speed reducers R31 to R36 that reduce the speeds of the outputs of servomotors M31 to M36 to increase their torques. Note that in FIG. 9, among the control systems for joints J31 to J36, the control systems for torsional joint J31 and torsional joint J36 are representatively illustrated, and illustration of the control systems for other joints J33 to J35 is omitted. Note that encoders E31 to E36 are provided as an example of rotational-position detectors that detect the rotational positions (rotational angles) of servomotors M31 to M36.

Rotational-position detectors such as resolvers may be used in place of encoders E31 to E36. Also, the above-mentioned elements of the drive systems for arm body 30 and cables and control units for them are made of high-temperature resistant materials and have heat resistance for sterilization.

In torsional joint J31, coupling base 80 and first link 81, servomotor M31 is provided at the base end portion of first link 81 and speed reducer R31 is provided at the tip portion of base 80. Speed reducer R31 in this embodiment is of a unit type including a gear that reduces the rotational speed of inputted power and an output gear that receives that output. Servomotor M31 is disposed with its output shaft in parallel to the rotation axis of torsional joint J31. Encoder E31 is attached to servomotor M31. The output of servomotor M31 is inputted into speed reducer R31. The output gear of speed reducer R31 is fixed to first link 81. Thus, first link 81 rotates relative to base 80 with the output from speed reducer R31.

In torsional joint J32, coupling first link 81 and second link 82, servomotor M32 is provided at the tip portion of first link 81, and speed reducer R32 is provided at the base end portion of second link 82. Servomotor M32 is disposed with its output shaft in parallel to the rotation axis of torsional joint J32. Encoder E32 is attached to servomotor M32.

In bend joint J33, coupling second link 82 and third link 83, speed reducer R33 is provided at the tip portion of second link 82, and servomotor M33 is provided at the base end portion of third link 83. Servomotor M33 is disposed with its output shaft in parallel to the rotation axis of bend joint J33. Encoder E33 is attached to servomotor M33.

In other joints J34 to J36 too, servomotors M34 to M36, encoders E34 to E36, and speed reducers R34 to R36 are disposed as above.

As servomotors M31 to M36 are employed servomotors small in output (e.g. about 80 W), weight, and size. Also, as speed reducers R31 to R36 are employed speed reducers having a flat shape with a small dimension in the axial direction and being capable of obtaining a high torque with a high speed reduction ratio (e.g. 100 or greater). High-output servomotors are not necessary for arms 3 of patient-side system 1 since arms 3 are not required to make high-speed motions like general industrial manipulators. Thus, servomotors M31 to M36 with relatively low outputs and speed reducers R31 to R36 with relatively high speed reduction ratios are used in combination with each other. In this way, necessary torques are ensured and arms 3 are made smaller in weight and size at the same time.

In addition, in a general industrial manipulator, the output of its servomotor is transferred to an output gear, a speed reducer, and a load in this order. However, in each arm 3 according to this embodiment, the output of its servomotor is transferred to a speed reducer, an output gear, and a load in this order. Arm 3 is also made smaller in weight and size by arranging the speed reducer on the input side relative to the output gear.

Controller 6 includes arm-body control unit 602 that controls the motion of arm body 30. Servo-control units C31 to C36 are electrically connected to arm-body control unit 602, and servomotors M31 to M36 are electrically connected to servo-control units C31 to C36 via amplification circuits and the like not illustrated. Controller 6 can communicate with data center 201 via in-facility network 202 or external network 203.

In the above-described configuration, a position-posture command for the tip portion of arm body 30 is inputted into arm-body control unit 602 based on a motion command inputted into manipulation apparatus 2. Arm-body control unit 602 generates position command values based on the position-posture command and the rotational angles detected by encoders E31 to E36, and output them. Acquiring these position command values, servo-control units C31 to C36 generate drive command values (torque command values) based on the rotational angles detected by encoders E31 to E36 and the position command values, and output them. Acquiring these drive command values, the amplification circuits feed drive currents corresponding to the drive command values to servomotors M31 to M36. Thus, servomotors M31 to M36 are servo-controlled such that the tip portion of arm body 30 reaches the position and the posture corresponding to the position-posture command.

Controller 6 transmits data on components that serves as movable parts of arms 3 (e.g. joints J31 to J36) to data center 201. Controller 6 transmits the following data, for example, to data center 201 via in-facility network 202 or external network 203.

The position command values outputted to servo-control units C31 to C36

The drive command values (torque command values) outputted from servo-control units C31 to C36

The current values of the drive currents fed from the amplification circuits

The temperatures collected by the temperature sensors disposed at servomotors M31 to M36

The encoder values of encoders E31 to E36 corresponding to the drive currents

The voltage values of the backup batteries for encoders E31 to E36

The electric resistance values of the harnesses provided in joints J31 to J36

Controller 6 can transmit image data captured by endoscope assembly 41 to data center 201. Controller 6 may transmit still image data captured by endoscope assembly 41 to data center 201. Controller 6 may transmit video data captured by endoscope assembly 41 to data center 201 as streaming data.

Controller 6 can transmit image data on arms 3 captured by at least one camera (not illustrated) provided to surgery system 100 to data center 201. Controller 6 acquires the image data from the camera and transmits the acquired data to data center 201. The camera can capture a still image of arms 3, and controller 6 can transmit the captured still image data to data center 201. Also, the camera can capture the motions of arms 3 in a video, and controller 6 can transmit the captured video data to data center 201.

Controller 6 transmits the above-mentioned information to data center 201 in association with the identification information (component IDs) of the components that serve as the movable parts of arms 3 (e.g. joints J31 to J36).

The data to be transmitted by controller 6 to data center 201 is not limited to the above-described example. Controller 6 can transmit the above-described data to data center 201 each time a motion command is inputted from manipulation apparatus 2.

[Structure for Coupling Arms and Platform]

The structure for coupling platform 5 and arms 3 is described.

Bases 80 of arms 3 are freely attachable to and detachable from platform 5. In other words, whole arms 3 can be easily detached from and attached to patient-side system 1. In this embodiment, four arms 3 are attachable to and detachable from platform 5. However, at least one of arms 3 of patient-side system 1 may only be attachable to and detachable from platform 5.

Arms 3 detached from patient-side system 1 undergo cleaning and sterilization and are then utilized again up to a limited number of times. Arms 3 are thus changed to sterilized, clean arms after each surgery. For this reason, arms 3 may not be covered with sterile drapes but exposed to the sterile field, as in the conventional practice.

Figure 11:
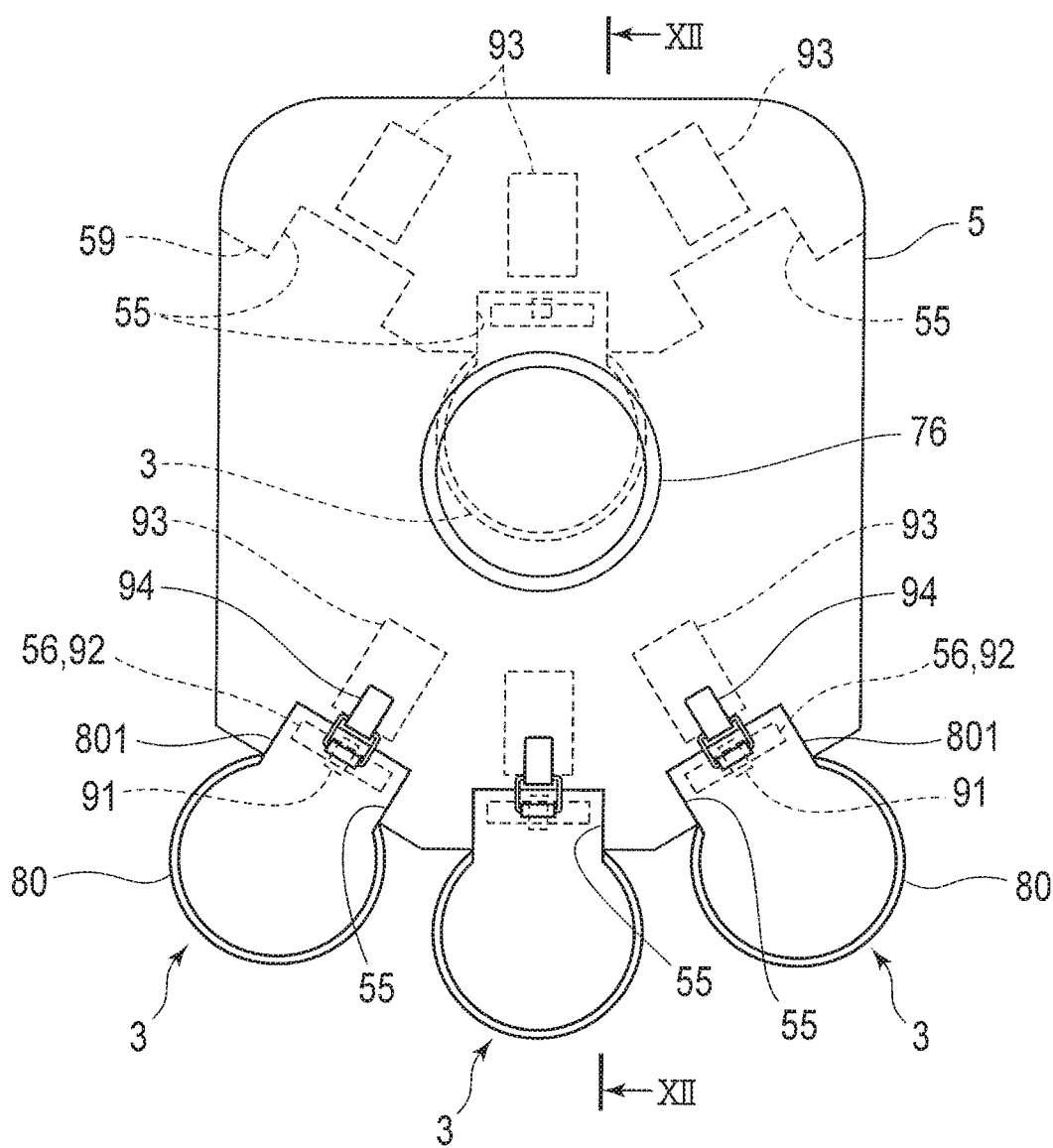
FIG. 11 is a plan view illustrating a structure for coupling the platform and patient-side manipulator arms.
Figure 12:
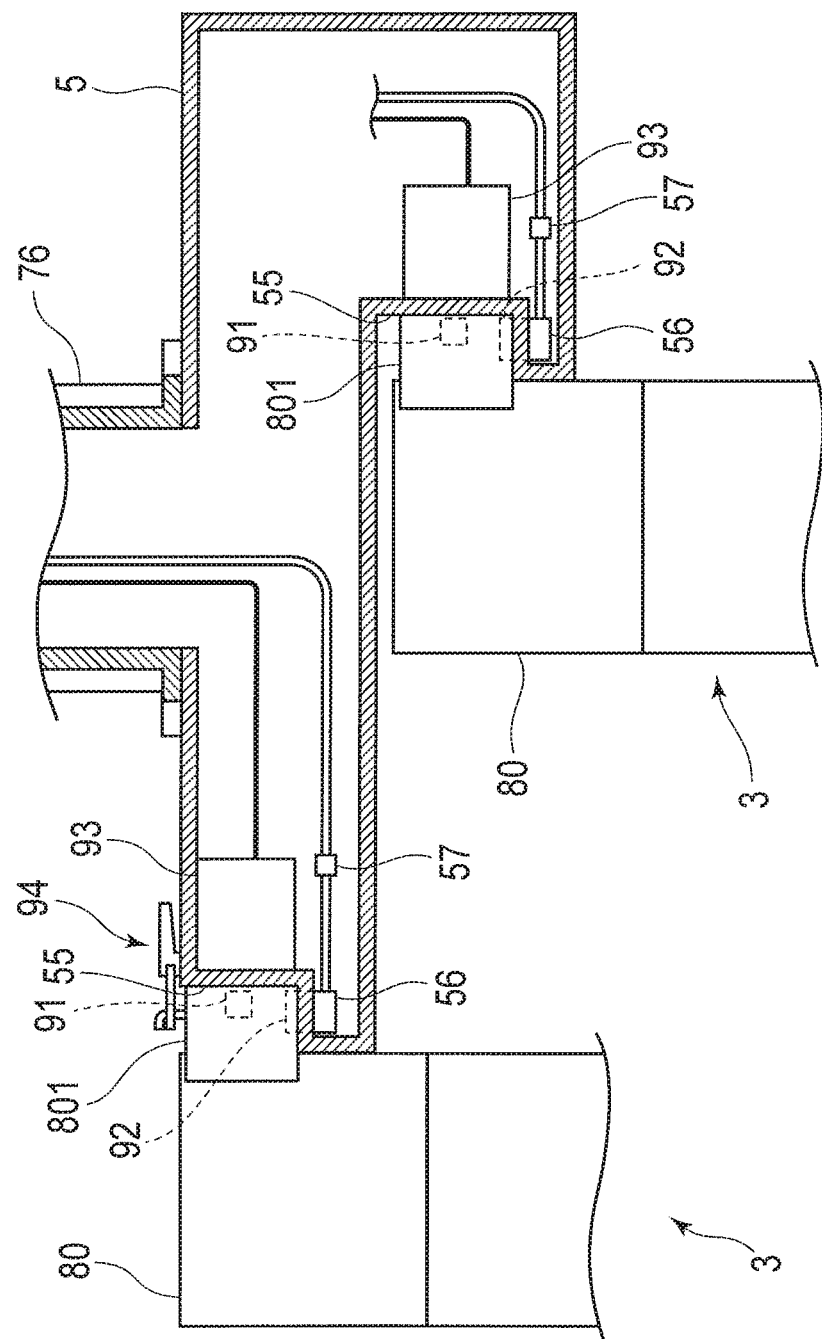
FIG. 12 is a cross-sectional view taken along line XII-XII in FIG. 11 and seen in the direction of arrows XII in FIG. 11.

FIG. 11 is a plan view illustrating the structure for coupling platform 5 and arms 3. FIG. 12 is a cross-sectional view taken along line XII-XII in FIG. 11 and seen in the direction of arrows XII in FIG. 11. As illustrated in FIG. 11 and FIG. 12, a base end portion of base 80 of each arm 3 is in a cylindrical shape and includes at least one interface section (hereinafter, also referred to as "I/F section 801") on its periphery or base end surface. I/F section 801 according to this embodiment is a protrusion formed on the outer peripheral surface of base 80. However, I/F section 801 is not limited to this type.

IC tag 91 is buried in I/F section 801 so as to provide arm 3 with identification information and the like. IC tag 91 includes an IC chip and an antenna, and the IC chip includes a microcomputer, an EEPROM, an RAM, and the like (none of them are illustrated). IC tag 91 stores individual identification information, model number, usage count, and the like of arm 3.

I/F section 801 is provided with one or more connectors 92. The one or more connectors 92 include a connector of a power cable for feeding electric power to arm 3, a connector of a communication cable for transmitting and receiving signals to and from arm 3, and the like.

Since four arms 3 are detachably attached to platform 5 in this embodiment, at least four attachment ports 55 are provided in platform 5. Platform. 5 is in a hexagonal shape which is a rectangular shape with two adjacent corners chamfered in a plan view, and three continuous side surfaces of this hexagonal shape have components oriented along the same direction. One attachment port 55 is provided in each of these three side surfaces. Moreover, the bottom of platform 5 is partially cut away to form wall 59 facing laterally. Like above-mentioned three attachment ports 55 on the upper side, three attachment ports 55 are provided on the lower side in this wall 59. In this embodiment, one of three attachment ports 55 on the lower side is used, and the other two are left unused. Thus, multiple attachment ports 55 are provided in platform 5, and attachment ports 55 to be used can be selected for each surgery.

As described above, I/F sections 801, provided on bases 80 of arms 3, and attachment ports 55, provided in platform 5, form a coupling mechanism for coupling arms 3 and platform 5. Moreover, bases 80 (i.e. arms 3) are attached to platform 5 when I/F sections 801 of bases 80 are fitted into attachment ports 55 of platform 5.

In each attachment port 55 of platform 5, socket 56 is provided at a position corresponding to connector 92, which is provided to I/F section 801. Connector 92 and socket 56 are automatically connected as I/F section 801 and attachment port 55 are coupled. A power cable and/or a communication cable is connected to socket 56 through spaces inside hollow elements (shafts and links) that form platform 5 and positioner 7. Note that connector 92 is exposed at the surface of arm 3 and is capable of contacting socket 56. Alternatively, a configuration may be employed in which connector 92 is buried in arm 3 to near its surface, and socket 56 and connector 92 are electrically connected to each other without contact therebetween by means of electromagnetic induction or the like.

Platform 5 is provided with reader-writer 93 that reads and writes (stores) the information of IC tag 91, which is buried in arm 3. This reader-writer 93 is provided for each attachment port 55 of platform 5, and outputs the information read from IC tag 91 to later-described controller 6. Reader-writers 93 that individually read IC tags 91 of respective arms 3 attached to platform 5 may be provided. Alternatively, reader-writer 93 that reads IC tags 91 of all arms 3 attached to platform 5 at once may be provided.

Platform 5 and each base 80 are provided with one or more attachment lock mechanism 94 capable of locking (holding) attachment of arm 3 to platform 5 to prevent base 80 from falling from platform 5, and of unlocking (releasing) the attachment of arm 3. Note that locking the attachment refers to fixing I/F section 801 of arm 3 attached to attachment port 55 of platform 5 to this attachment port 55, and unlocking the attachment refers to releasing the fixation.

Attachment lock mechanism 94 is formed as a combination of a member provided at or near attachment port 55 of platform 5 and a member provided at or near I/F section 801 of arm 3. Such attachment lock mechanism 94 is selected for example from a group of members including: a protrusion provided to one of platform 5 and base 80 and a lever with a latch provided to the other; a recess provided to one of platform 5 and base 80 and an engagement claw provided to the other; and a recess provided to one of platform 5 and base 80 and a ball plunger provided to the other. Alternatively, attachment lock mechanism 94 may be another publicly known attachment lock mechanism. Nonetheless, attachment lock mechanism 94 is desirably one that can lock and unlock the attachment with one simple action, instead of one that requires use of a tool for locking and unlocking the attachment, such as a bolt and a nut.

Figure 13:
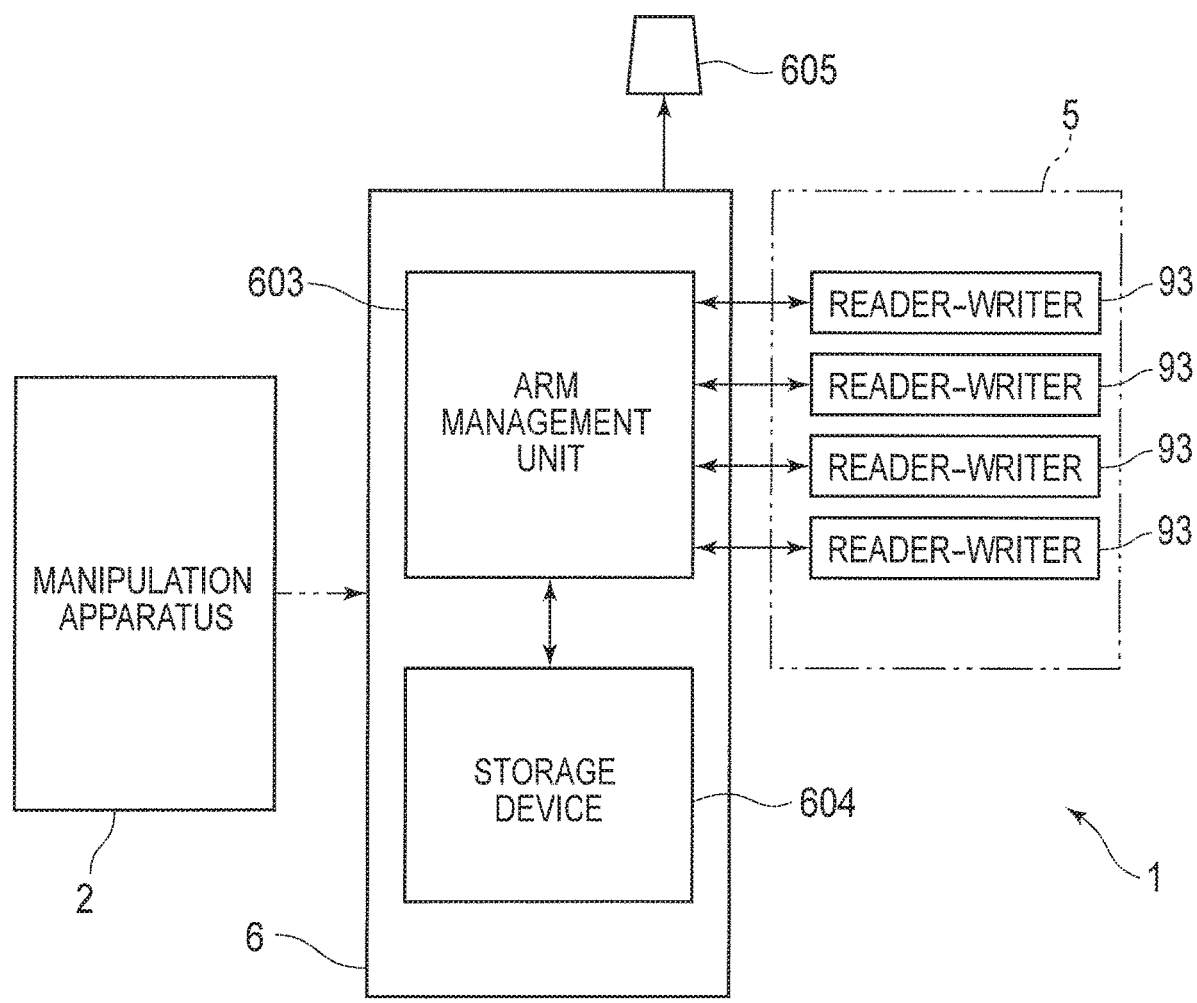
FIG. 13 is a block diagram illustrating a configuration for managing the patient-side manipulator arms attached to the platform.

FIG. 13 is a block diagram illustrating a configuration for managing arms 3 attached to platform 5. As illustrated in FIG. 13, controller 6 includes arm management unit (management device) 603 that manages arms 3 attached to platform 5. Reader-writers 93 are electrically connected to arm management unit 603. Controller 6 can communicate with data center 201 via in-facility network 202 or external network 203.

Arm management unit 603 detects when connectors 92 and sockets 56 are connected to each other, based on feed of electric power from platform 5 to arms 3. The feed of electric power from platform 5 to arms 3 can be detected based on detection signals from current detection sensors (detection sensors 57) provided on the power cables or communication cables extending to sockets 56, for example. When connectors 92 and sockets 56 are connected, it means that I/F sections 801 are properly attached to attachment ports 55. In sum, it is possible to detect the presence of arms 3 attached to attachment ports 55, based on whether or not electric power is being fed from platform 5 to arms 3. Thus, arm management unit 603 can detect attachment of arm 3 for each attachment port 55 of platform 5.

Alternatively, platform 5 may be provided with contact-type or contactless-type object detection sensors (not illustrated) to detect the presence of arms 3 attached to attachment ports 55. In this case, arm management unit 603 detects attachment of arms 3 to attachment ports 55 based on detection signals from these detection sensors.

Upon detection of attachment of arms 3 to attachment ports 55, arm management unit 603 causes reader-writers 93 to perform reading operations and, based on the information read from IC tags 91 by reader-writers 93, acquires the individual identification information, the model number information (type), the usage count information, and the like of each arm 3 connected to platform 5. Arm management unit 603 temporarily stores the acquired pieces of information in association with information on the position of attachment of that arm 3 on platform 5 (i.e. attachment port 55). Note that attachment ports 55 are identified individually. IC tags 91 may store information on expendable parts of endoscope assembly 41 and instruments 42 attached to arms 3. For example, IC tags 91 may store the usage time of the endoscope lamp in endoscope assembly 41, the usage time of forceps as instrument 42, and the like.

Controller 6 transmits the information read from IC tags 91 by arm management unit 603 to data center 201. Controller 6 transmits, for example, the individual identification information, the model number information (type), and the usage count information of each arm 3 to data center 201. Controller 6 transmits the individual identification information, the model number information (type), and the usage count information of each arm 3 to data center 201 in association with the identification information of surgery system 100. Controller 6 may transmit the information on the expendable parts of endoscope assembly 41 and instruments 42 to data center 201. For example, controller 6 transmits the usage time of the lamp in endoscope assembly 41 and the usage time of forceps as instrument 42 to data center 201.

Also, surgery information has been inputted and set (stored) in advance in controller 6 via manipulation apparatus 2. This surgery information includes the combination of arms 3 to be used in the surgery.

Arm management unit 603 determines whether or not the combination of the pieces of individual identification information contained in the pieces of information acquired from reader-writers 93 matches the one set as the above-mentioned surgery information. If the combination does not match the one set as the surgery information, arm management unit 603 outputs a warning via alarm 605, connected to controller 6. Note that alarm 605 warns operator O by using one or more of light, sounds, and images. Arm management unit 603 manages arms 3 to be attached to platform 5 in this manner so as to attach proper arms 3.

The above-mentioned surgery information may contain information on the combination of the individual identification information of each arm 3 to be used in the surgery and the position on platform 5 (i.e. attachment port 55) at which that arm 3 should be attached.

In this case, arm management unit 603 determines whether or not the combination of the individual identification information contained in the information acquired from reader-writer 93 and the information on the position of attachment on platform 5 (i.e. attachment port 55) stored in association therewith matches the one set in the above-mentioned surgery information. If the combination does not match the one set in the surgery information, arm management unit 603 outputs a warning via alarm 605, connected to controller 6. In this way, arm management unit 603 manages arms 3 to be attached to platform 5 such that arms 3 are attached at the appropriate positions on platform 5 and appropriate arms 3 are attached to attachment ports 55.

Also, the surgery information may contain information on the combination of the model number information of each arm 3 to be used in the surgery and the position on platform 5 (i.e. attachment port 55) at which that arm 3 should be attached.

In this case, arm management unit 603 determines whether or not the combination of the model number information contained in the information acquired from reader-writer 93 and the position of attachment (i.e. attachment port 55) associated therewith matches the one set in the above-mentioned surgery information. If the combination does not match the one set in the surgery information, arm management unit 603 may output a warning via alarm 605, connected to controller 6.

Arms 3 differ from each other in type (camera arm 3A, instrument arm 3B), structure (such as the link length and the degree of freedom), and the like depending on the model number. In the above case, IC tags 91 store the pieces of model number information. However, storage device 604 may include a model-number storage unit that stores the pieces of model number information in association with the pieces of individual identification information. Then, based on pieces of individual identification information, arm management unit 603 may read the corresponding pieces of model number information from the model-number storage unit, and these pieces of model number information may be used in place of the pieces of model number information read from IC tags 91 in the above-described processing.

Controller 6 may receive the above-described surgery information from data center 201. Controller 6 may perform the above-described control based on the surgery information received from data center 201.

Storage device 604 of controller 6 includes a usage-count-limit storage unit that stores usage count limits associated with the pieces of individual identification information. Based on the individual identification information acquired from each IC tag 91, arm management unit 603 reads the corresponding usage count limit from storage device 604 and compares the usage count limit and the acquired usage count information. If the usage count information is greater than the usage count limit, arm management unit 603 outputs a warning via alarm 605, connected to controller 6. Arm management unit 603 manages the usage count of each arm 3 in this manner so as to prevent the arm from being used over the usage count limit. Note that after its usage count reaches the limit, each arm 3 is collected by a manufacturer. After instrument 42, which is an expendable part, is detached from collected arm 3, arm 3 is cleaned. New instrument 42 and IC tag 91 are attached to arm 3, and arm 3 is sterilized and can be used again.

Arm management unit 603 actuates reader-writers 93 to overwrite IC tags 91 with new usage count information obtained by adding one to the pieces of usage count information acquired from IC tags 91. Consequently, each arm 3 holds information on the usage count of itself in its IC tag 91. In this way, patient-side system 1 can share arms 3 with other patient-side systems 1.

In the above case, each arm 3 holds the usage count information on itself. However, storage device 604 of controller 6 may store the usage count information on each arm 3. In this case, readers having only a reading function may be used in place of reader-writers 93. Based on the pieces of individual identification information read from IC tags 91 by the readers, arm management unit 603 may read the corresponding pieces of usage count information from storage device 604 and utilize them for the above-described processing.

While a preferred embodiment of the structure for coupling platform 5 and arms 3 has been described above, the above-described structure for coupling platform 5 and arms 3 can be changed as below, for example.

For example, in the above-described embodiment, six attachment ports 55 are provided in platform 5, and arms 3 are coupled to four of these attachment ports 55. Thus, there may be an unused attachment port(s) 55 among multiple attachment ports 55. Alternatively, five or more attachment ports 55 may be provided in platform 5, and attachment ports 55 at positions suitable for the content of surgery may be selectively used.

For example, in the above-described embodiment, each arm 3 is provided with IC tag 91 so that arm 3 itself can possess its information. However, IC tag 91 is an example of an information holder provided to arm 3, and a different information holder may be used in place of or in addition to IC tag 91. In one example, each arm 3 may be provided with a barcode, and platform 5 may be provided with barcode readers. In another example, each arm 3 may be provided with a shaped code such as recesses and protrusions, and platform 5 may be provided with readers that read the shaped code.

In the above-described embodiment, connector 92 is provided at I/F section 801 of base 80 of each arm 3, and socket 56 is provided at each attachment port 55 of platform 5, but connector 92 and socket 56 may be omitted. In this case, the power cable for electric power feed and/or the cable for communication are connected to arm 3 at a position other than I/F section 801.

[Example Configuration of Data Center]

Figure 14:
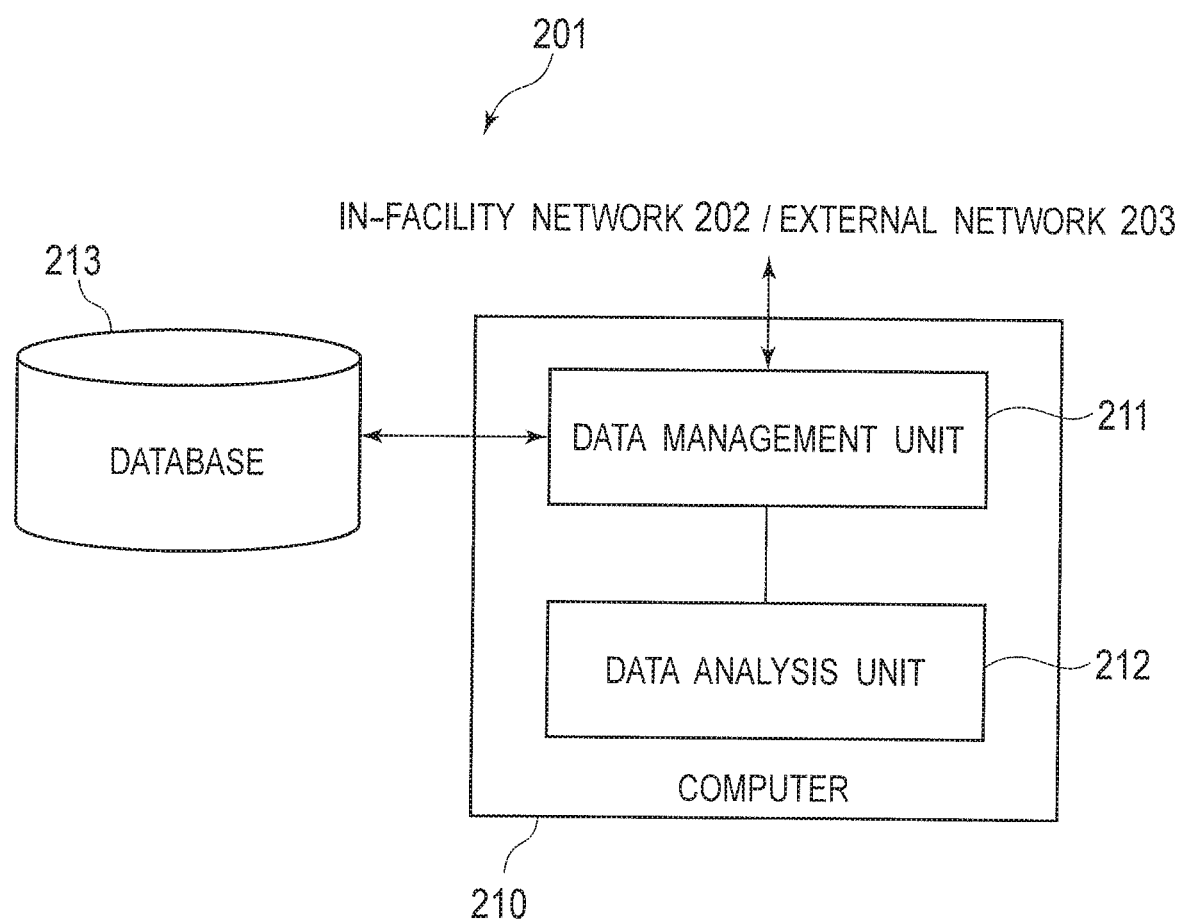
FIG. 14 illustrates a configuration diagram of a data center according to an embodiment.

FIG. 14 illustrates an example configuration of data center 201. Data center 201 includes computer 210 and database 213. Computer 210 includes data management unit 211 and data analysis unit 212. Data management unit 211 communicates with the surgery robots of surgery systems 100 via in-facility network 202 or external network 203. The computer 210 serves as a data analysis apparatus.

Data management unit 211 stores data received from surgery robots into database 213. Data management unit 211 transmits data read from database 213 to surgery robots.

Data analysis unit 212 monitors surgery robots in operation through a statistic analysis of the data stored in database 213. Details of the analysis operation are described later. Data analysis unit 212 notifies the result of the monitoring to support center 205 via external network 203. Data analysis unit 212 may notify the monitoring result, for example, to manipulation apparatus 2 via in-facility network 202.

Data analysis unit 212 may be provided in advance with solutions programmed based on robot technicians' knowledge.

FIGS. 15A and 15B illustrate examples of the format of data transmitted and received between a surgery robot and data center 201.

In the example of FIG. 15A, the data format includes system ID 220 as identification information of the surgery robot in surgery system 100, component ID 221 as identification information of a movable part of arm 3 or positioner 7, monitoring-target data 222 on the movable part of arm 3 or positioner 7, and timestamp 223 as the time at which monitoring-target data 222 is collected. Monitoring-target data 222 is the encoder value, the current value of the servomotor, or the like as mentioned above.

In a case of collecting multiple types of data from each single movable part, the data format may include data ID 224 indicating the data type, as illustrated in the example of FIG. 15B.

FIG. 16 illustrates a data format with which information collected from IC tag 91 of arm 3 is transmitted and received between the surgery robot and data center 201.

The data format includes system ID 220, individual identification information 230 of arm 3, model number information 231 corresponding to the type of the arm, usage count 232 of arm 3, and attachment port ID indicating attachment port 55 to which arm 3 is attached.

[Data Analysis Example (1)]

Data analysis unit 212 can perform a data analysis for prevention of abnormalities, failures, and the like in surgery system 100 by using the data stored in database 213. Data analysis unit 212 can also perform a data analysis for provision of backup support during a surgery by using data successively stored into database 213 during the surgery.

The prevention of abnormalities, failures, and the like is to ensure high safety by quickly taking action not when detecting a failure is detected but when finding a possibility that will lead to the failure, based on the information stored in database 213.

Data analysis unit 212 can monitor monitoring-target data 222 on components which are the movable parts of arms 3 and positioner 7, and detect signs of future abnormalities and failures of arms 3 and positioner 7. Data analysis unit 212 monitors following monitoring-target data 222 on arms 3 and positioner 7, for example.

The position command values outputted to the servo-control units

The drive command values (torque command values) outputted from the servo-control units The current values of the drive currents fed from the amplification circuits The temperatures collected by the temperature sensors disposed at the servomotors The encoder values of the encoders corresponding to the drive currents The voltage values of the backup batteries for the encoders The electric resistance values of the harnesses provided in the joints Image and video data from endoscope assembly 41 (images of states from the internal device of the endoscope)

Image and video data captured by the camera installed in surgery system 100

Information on expendable parts (usage count and usage time)

Distances measured by laser sensors

When the difference between monitoring-target data 222 on a component and a normal value exceeds a predetermined threshold, data analysis unit 212 can determine that as a sign of a future abnormality or failure of arm 3 or positioner 7. For example, data analysis unit 212 compares the temperature data on a servomotor and a normal value and, when the difference between the temperature data and the normal value exceeds a predetermined threshold, determines that as a sign of a future abnormality or failure of arm 3.

Data analysis unit 212 can determine the presence of a sign of a future abnormality or failure of arm 3 or positioner 7 based on the number of times the difference between monitoring-target data 222 on the component and the normal value exceeds the predetermined threshold. When the number of times the difference between the monitoring-target data on the component and the normal value exceeds the predetermined threshold reaches or exceeds a predetermined number of times, data analysis unit 212 can determine that as a sign of a future abnormality or failure of arm 3 or positioner 7. For example, data analysis unit 212 monitors the number of times the difference between the electric resistance value of a harness and a normal value exceeds a predetermined threshold and, when the number of times reaches or exceeds a predetermined number of times, determines that as a sign of a future abnormality or failure of arm 3 or positioner 7.

Data analysis unit 212 can determine the presence of a sign of a future abnormality or failure of arm 3 or positioner 7 based on the length of time for which the difference between monitoring-target data 222 on the component and the normal value exceeds the predetermined threshold. Data analysis unit 212 monitors the length of time for which the difference between the monitoring-target data on the component and the normal value exceeds the predetermined threshold, by using timestamp 223 stored in database 213. When the period in which the difference between monitoring-target data and the normal value exceeds the predetermined threshold continues for a predetermined length of time, data analysis unit 212 can determine that as a sign of a future abnormality or failure of arm 3 or positioner 7. For example, data analysis unit 212 monitors the length of time for which the difference between the current value of the servomotor and a normal value exceeds a predetermined threshold and, when this period continues for a predetermined length of time, can determine that as a sign of a future abnormality or failure of arm 3 or positioner 7.

Data analysis unit 212 can detect a sign of a future abnormality or failure of arm 3 or positioner 7 based on multiple pieces of monitoring-target data 222 acquired from movable parts. Data analysis unit 212, for example, monitors the current value of the servomotor and the encoder value for the current value. Data analysis unit 212 monitors the difference between an encoder value expected from the current value (expected value) and the monitored encoder value. When the difference exceeds a predetermined threshold, data analysis unit 212 determines that as a sign of a future abnormality or failure of arm 3 or positioner 7. Data analysis unit 212 may determine the presence of a sign of a future abnormality or failure of arm 3 or positioner 7 based on the number of times the difference exceeds the predetermined threshold or the length of time for which the difference exceeds the predetermined threshold.

Data analysis unit 212 can dynamically generate a reference to be used to detect a sign of a future abnormality or failure of arm 3 or positioner 7, based on multiple pieces of monitoring-target data 222. For example, data analysis unit 212 changes the reference for detection of a sign of failure of arm 3 or a future abnormality of the current value to be fed to a servomotor, in accordance with the three-dimensional position of arm 3 or positioner 7 calculated from its encoder values. For example, when arm 3 is situated substantially horizontally relative to the floor on which operating table 111 is installed, data analysis unit 212 sets a higher reference value for detection of a sign of a future abnormality of the current value or failure of arm 3 than when the tip portion of arm 3 is facing toward the floor.

Data analysis unit 212 can detect a sign of a future abnormality or failure of arm 3 or positioner 7 based on pieces of monitoring-target data 222 acquired from multiple surgery robots.

For example, data analysis unit 212 can detect a sign of a future abnormality or failure of arm 3 or positioner 7 based on a statistical analysis on the pieces of monitoring-target data 222 on movable parts classified as the same type acquired from multiple surgery robots (e.g. torsional joints of arms 3 of the surgery robots and bend joints of arms 3 of the surgery robots). Data analysis unit 212 calculates the mean (M) and the standard deviation (σ) of the group of pieces of monitoring-target data 222 on the movable parts classified as the same type. Data analysis unit 212 calculates the mean and the standard deviation for each group of movable parts classified as the same type. Data analysis unit 212 uses the following inequality, for example, as a reference for detection of a sign of a future abnormality or failure of arm 3 or positioner 7.

$$|X-M|>3\sigma$$

In the above inequality, X denotes monitoring-target data 222 acquired from arm 3 or positioner 7 in operation. Based on the above inequality, when the absolute value of the difference between monitoring-target data 222 and the mean (M) is greater than $3\sigma$, data analysis unit 212 determines that as a sign of a future abnormality or failure of arm 3 or positioner 7 with this monitoring-target data 222. Alternatively, when the absolute value of the difference between monitoring-target data 222 and the mean (M) is greater than $2\sigma$ or $4\sigma$, data analysis unit 212 may determine that as a sign of a future abnormality or failure of arm 3 or positioner 7 with this monitoring-target data 222. Data analysis unit 212 updates the above-described reference at a predetermined interval, for example.

Data analysis unit 212 may calculate the above-described reference based on a statistical analysis on the pieces of monitoring-target data 222 on identical movable parts acquired from multiple surgery robots (e.g. torsional joints J31 of arms 3 of the surgery robots and bend joints J33 of arms 3 of the surgery robots).

As described above, data analysis unit 212 can dynamically generate a reference for detection of a sign of a future abnormality or failure based on a number of pieces of monitoring-target data 222 acquired from multiple surgery robots. Since a sign of a future abnormality or failure can be detected using a reference generated based on a number of pieces of monitoring-target data 222, accurate determination is possible as compared to the case of monitoring a piece of monitoring-target data 222 from a single surgery robot.

Data analysis unit 212 may detect a sign of a future abnormality or failure of arm 3 or positioner 7 based on the correlation between different pieces of monitoring-target data 222.

Data analysis unit 212 can detect an abnormality resulting from interference between arms 3. When arms 3 interfere with each other, arms 3 exhibit motions that are not based on the command from manipulation apparatus 2. Each surgery robot figures out the behavior of each arm 3 by comparing each of its encoder values based on the position command values from manipulation apparatus 2 and an origin position. Any unexpected motion of arm 3 caused by interference with another arm 3 is not reflected on the encoder values, thereby causing a difference between the position of arm 3 corresponding to the encoder values and the actual position of arm 3. In this case, an attempt to bring arm 3 back to the origin fails, that is, arm 3 cannot be brought back to the right origin position, due to the difference occurring between the position of arm 3 corresponding to the encoder values and the actual position of arm 3. Data analysis unit 212, for example, analyzes image or video data to figure out the position of arm 3 shifted by the interference, and corrects the shift of the origin accordingly. Data analysis unit 212, for example, analyzes image or video data to figure out the position of arm 3 shifted by the interference, and calculates the difference between it and the position of arm 3 corresponding to its encoder values. Data analysis unit 212 calculates encoder values corresponding to the calculated difference, and calculates correction values for the shift of the origin based on the calculated encoder values. Data analysis unit 212 notifies the calculated correction values to support center 205 or the surgery robot.

Data analysis unit 212 notifies warning information to support center 205 when detecting a sign of a future abnormality or failure of arm 3 or positioner 7. The notification of the warning information from data analysis unit 212 is, for example, displayed on the monitor of a terminal used by a service person at support center 205. Based on the notification displayed on the monitor, the service person notifies a warning or an operation stop command to the surgery robot from which the sign of a future abnormality or failure has been detected. Based on the notification displayed on the monitor, the service person may support the user of the surgery robot by telephone or send a maintenance person. The service person can connect the monitor of the terminal and the monitor 53 of the surgery robot and display a screen for manipulating the surgery robot on the monitor of the terminal. The service person can remotely manipulate the surgery robot via the manipulation screen displayed on the monitor of the terminal.

Data analysis unit 212 may constantly transmit the result of the monitoring of monitoring-target data 222 to support center 205. The monitoring result is successively displayed on the monitor of the terminal used by the service person at support center 205. For example, data analysis unit 212 constantly transmits the difference between each piece of monitored data 222 acquired from a surgery robot in a surgery and the normal value to support center 205. The service person monitors the information transmitted from data analysis unit 212 to determine the presence of a sign of a future abnormality or failure of arm 3 or positioner 7. The service person can connect the monitor of the terminal and monitor 53 of the surgery robot and display the screen for manipulating the surgery robot on the monitor of the terminal. The service person can remotely manipulate the surgery robot via the manipulation screen displayed on the monitor of the terminal.

Data analysis unit 212 may directly notify warning information to the surgery robot without notifying it to support center 205 when detecting a sign of a future abnormality or failure of arm 3 or positioner 7. Data analysis unit 212, for example, notifies a warning or an operation stop command to the surgery robot from which the sign of a future abnormality or failure has been detected.

Data analysis unit 212 may present a solution on the monitor of the terminal used by the service person.

Data analysis unit 212 can acquire the information on expendable parts (such as the usage count of each arm 3 and the usage time of the lamp in endoscope assembly 41) from database 213. Data analysis unit 212 compares reference values for replacement of the expendable parts and the pieces of information acquired from database 213. Data analysis unit 212, for example, notifies support center 205 that the usage count and the usage time acquired from database 213 have reached or exceeded the reference values. Based on the notification, the service person at support center 205 notifies the surgery robot that it is soon time for replacement of the expendable parts. Based on the notification, the service person may command a maintenance person to add or replace the expendable parts.

[Data Analysis Example (2)]

Data analysis unit 212 performs an analysis for checking and setup of a surgery robot before a surgery by using the data stored in database 213.

Support on the checking and setup before a surgery can automate checking of pre-surgery setup information for checking the operation of each part of the surgery robot before it is used. This support enables checking of the surgery robot from a remote location based on a robot technician's judgment.

Data analysis unit 212 can perform an operation check on arms 3 and positioner 7. Data analysis unit 212 can also perform an operation check on manipulation apparatus 2, endoscope assembly 41, and instruments 42.

Data analysis unit 212 analyzes the difference between each of the position command values outputted to the servo-control units and the encoder value for the position command value. Data analysis unit 212, for example, analyzes the difference between an encoder value expected from the position command value (expected value) and the actual encoder value. Data analysis unit 212 can, for example, analyze the difference between a current value expected from the position command value (expected value) and the actual current value to check the condition of arm 3 or positioner 7 in terms of torque. Also, data analysis unit 212 can, for example, rotate each servomotor with arm 3 braked, and analyze the current value at which the servomotor starts to rotate to check the brake torque.

Data analysis unit 212 notifies the result of the analysis to support center 205. The notification from data analysis unit 212 is, for example, displayed on the monitor of the terminal used by the service person at support center 205. Based on the notification displayed on the monitor, the service person commands the surgery robot to correct the difference. For example, the service person transmits a correction value for correcting the difference to the surgery robot.

Data analysis unit 212 may directly notify the analysis result to the surgery robot without notifying it to support center 205. Data analysis unit 212 may calculate a correction value for correcting the difference and transmit the calculated correction value to the surgery robot.

Data analysis unit 212 can check the accuracy of positioning of arms 3 and positioner 7 based on image or video data captured by a camera installed to endoscope assembly 41 or surgery system. 100. Data analysis unit 212 analyzes the image or video data to analyze whether arms 3 and positioner 7 have been moved to the positions corresponding to the position command values. Data analysis unit 212 virtually sets the positions corresponding to the position command values on the image data and analyzes whether or not arms 3 and positioner 7 have reached these positions. Data analysis unit 212 calculates the amounts of movement of arms 3 and positioner 7 corresponding to the position command values. Data analysis unit 212 analyzes the image or video data to determine whether or not arms 3 and positioner 7 have been moved by the calculated amounts of movement. Data analysis unit 212 can analyze the image or video data to also check the positions of arms 3 relative to each other.

Data analysis unit 212 can check the backlashes of arms 3 and positioner 7 based on image or video data captured by the camera installed to endoscope assembly 41 or surgery system 100. The backlashes refer to the gaps intentionally provided between the gears provided to arms 3 and positioner 7. The backlashes are assumed to change due to wear and deterioration of the gears. Data analysis unit 212 can analyze the change in the backlashes.

In the case where a backlash changes, a time lag occurs in the timing at which the corresponding joint of arm 3 or positioner 7 makes a motion after input of a position command value. Data analysis unit 212 analyzes video data to calculate the time lag in the timing at which the joint of arm 3 or positioner 7 makes a motion after input of a position command value.

Data analysis unit 212 notifies the result of the analysis to support center 205. Data analysis unit 212 notifies image or video data indicating the analysis result or data indicating the analysis result to support center 205. The notification from data analysis unit 212 is, for example, displayed on the monitor of the terminal used by the service person at support center 205. Based on the image or video data displayed on the monitor, the service person commands the surgery robot to correct the positioning difference or backlash change. For example, the service person transmits a correction value for correcting the difference or change to the surgery robot.

Data analysis unit 212 may directly notify the analysis result to the surgery robot without notifying it to support center 205. Data analysis unit 212 may calculate a correction value for correcting the difference or change and transmit the calculated correction value to the surgery robot.

Data analysis unit 212 can also check whether manipulation pedal 52, endoscope assembly 41, instruments 42 (e.g. an electrocautery (energy device), forceps, etc.), monitor 53, a recorder, and the like are properly connected to the surgery robot. Data analysis unit 212 can further check the operation of energy devices such as a monopolar electrocautery and a bipolar electrocautery. Through these checks, whether devices are bent and the like can be checked, for example. Furthermore, whether the devices used are the regular ones can be checked. This check can be done by providing a sensor or the like at an attachment portion of each surgical device. Checking of energy devices includes an operation check on a bipolar electrocautery (an electric scalpel with two tips, which causes high-frequency current to flow from one of the tips of the scalpel and collects it from the opposite tip of the scalpel) and the like (checking poor output, etc).

Data analysis unit 212 can generate information on the configuration of each arm 3. Data analysis unit 212 can support the user of the surgery robot by notifying the generated configuration information to the surgery robot via support center 205. Data analysis unit 212 may directly notify the generated configuration information to the surgery robot. The configuration information notified to the surgery robot is stored into controller 6 for arms 3 and positioner 7 as the above-mentioned surgery information. Data analysis unit 212 can save the configuration information into database 213 and utilize this information again.

Figure 17:
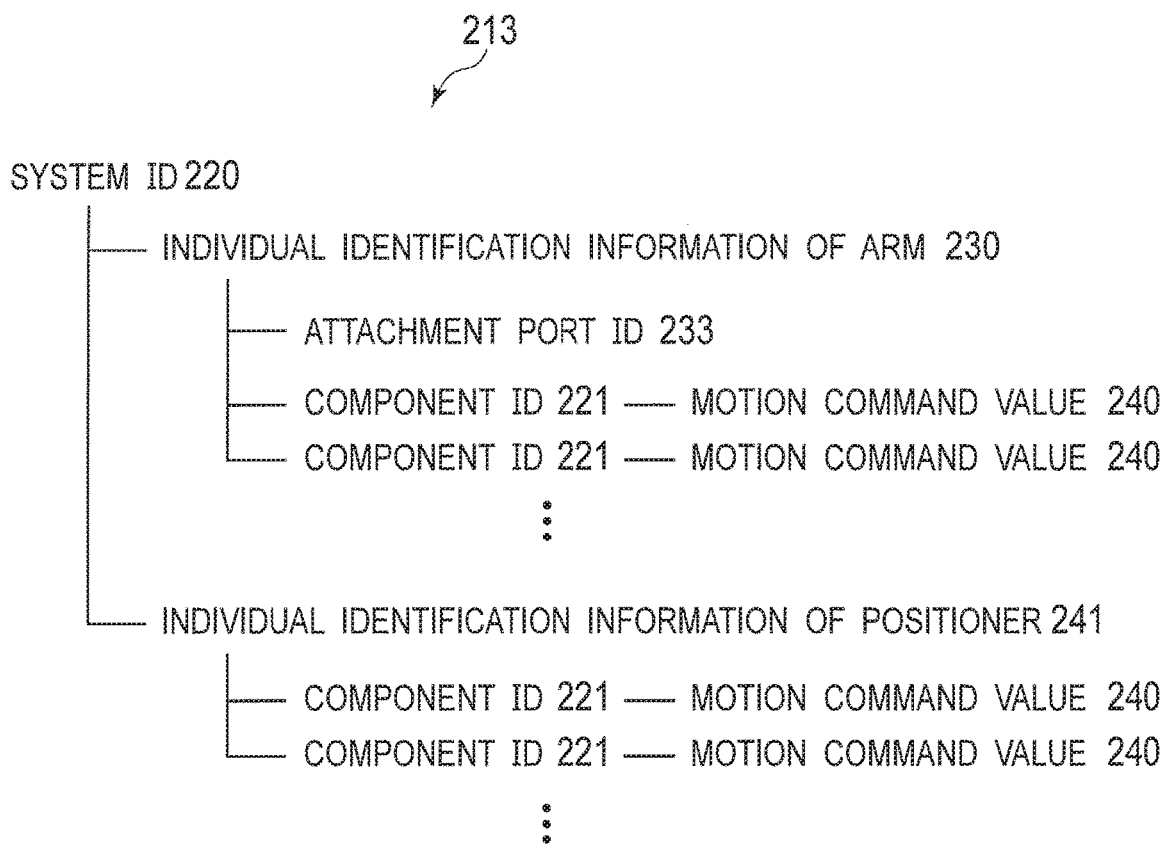
FIG. 17 is a diagram illustrating a data structure in the database according to an embodiment.

FIG. 17 illustrates an example of the configuration information, generated by data analysis unit 212. For example, based on the surgical method to be implemented by the surgery robot, data analysis unit 212 generates configuration information suitable for that surgical method. Information on the surgical method is notified to data analysis unit 212, for example, via manipulation apparatus 2 of the surgery robot. The information on the surgical method includes, for example, information on the positions of the sleeves (cannula sleeves) to be placed in the body of the patient and information on the positions of the patient and the bed relative to each other. Data analysis unit 212 can also generate the configuration information based on features of the doctor who is to use the surgery robot (e.g. the standing height, the sitting height, etc). Data analysis unit 212 may generate the configuration information based on the combination of the surgical method and the features of the doctor or other information.

In the configuration information, the configurations of arms 3 and the configuration of positioner 7 are set per system ID 220, for example.

The configuration of arm 3 is set per individual identification information 230 of arm. The configuration of arm 3 includes, for example, attachment port ID 233 and motion command value 240 for each component ID 221.

The configuration of positioner 7 is similar to the configuration of arm 3.

[Data Analysis Example (3)]

Data analysis unit 212 can analyze the histories of usage of endoscope assembly 41 and instruments 42 and states of usage of expendable parts by using data stored in database 213.

Database 213 can manage data on each customer based on information acquired from the surgery robots.

Figure 18:
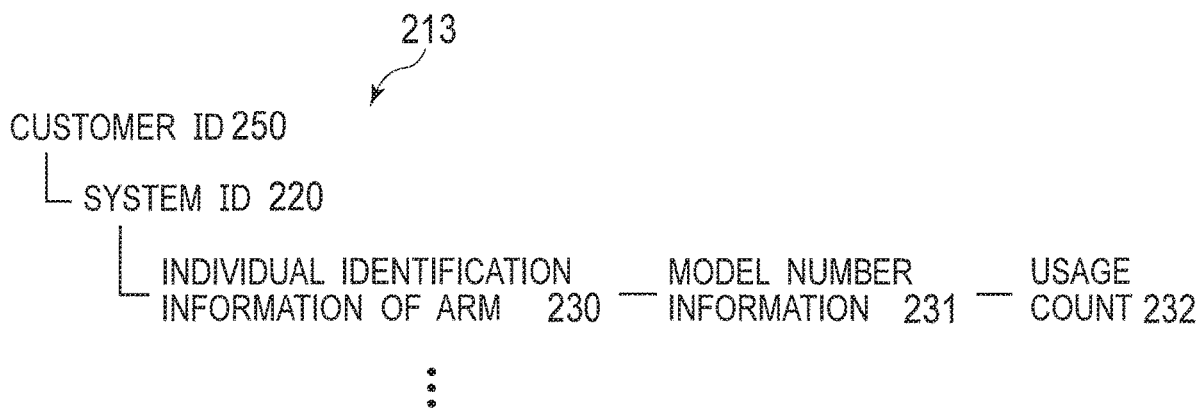
FIG. 18 is a diagram illustrating a data structure in the database according to an embodiment.

FIG. 18 illustrates an example of the customer management data in database 213. The customer management data contains information on the surgery robots that have been delivered to customers, arms 3 that have been delivered to customers, and the expendable parts that have been delivered to customers.

Database 213 manages customer IDs 250 for identifying customers and system IDs 220 of the surgery robots that have been delivered to these customers in association with each other. Database 213 manages the information on arms 3 and the information on the expendable parts of endoscope assembly 41 and instruments 42 in association with system IDs 220.

Data analysis unit 212 figures out the usage count of each arm 3, the usage time of each expendable part, and the like by referring to the customer management data, exemplarily illustrated in FIG. 18. Also, data analysis unit 212 can figure out the stock statuses of arms 3 and the expendable parts for each customer by referring to the customer management data, exemplarily illustrated in FIG. 18. Data analysis unit 212, for example, notifies the usage count of each arm 3, the usage time of each expendable part, and their stock statuses to support center 205.

The service person at support center 205, for example, checks the difference between the usage count limit and the current usage count and the difference between the usage time limit and the current usage time. The service person commands a maintenance person to add arms 3 or expendable parts in a case, for example, where the number of arms 3 or expendable parts with the above-mentioned difference greater than or equal to a predetermined value is greater than or equal to the amount of stock. The service person may command the production site of arms 3 or the expendable parts to ship arms 3 or the expendable parts in the case where the number of arms 3 or expendable parts with the above-mentioned difference greater than or equal to the predetermined value is greater than or equal to the amount of stock.

Data analysis unit 212 may command the maintenance person or the production site to add arms 3 or the expendable parts without notifying such information to support center 205. Data analysis unit 212 checks the difference between the usage count limit and the current usage count and the difference between the usage time limit and the current usage time. Data analysis unit 212 commands the maintenance person or the production site to add arms 3 or the expendable parts in the case, for example, where the number of arms 3 or expendable parts with the above-mentioned difference greater than or equal to the predetermined value is greater than or equal to the amount of stock.

The service person at support center 205 can also propose an efficient system operation method by accumulating data such as the work time for which surgery is performed with the surgery robot, the time of operation of the surgery robot, and the amount of operation of the surgery robot.

[Data Analysis Example (4)]

Data analysis unit 212 can generate simulation data for the surgery robots based on data acquired from the surgery robots. The generated simulation data may be utilized, for example, for education of the users of the surgery robots, researches at medical institutions, universities, etc., and the like.

Each surgery robot successively transmits monitoring-target data 222 on the motions of arms 3 and positioner 7 during surgery to data center 201. The surgery robot, for example, transmits monitoring-target data 222 to data center 201 in association with the information indicating the method of the surgery.

Figure 19:
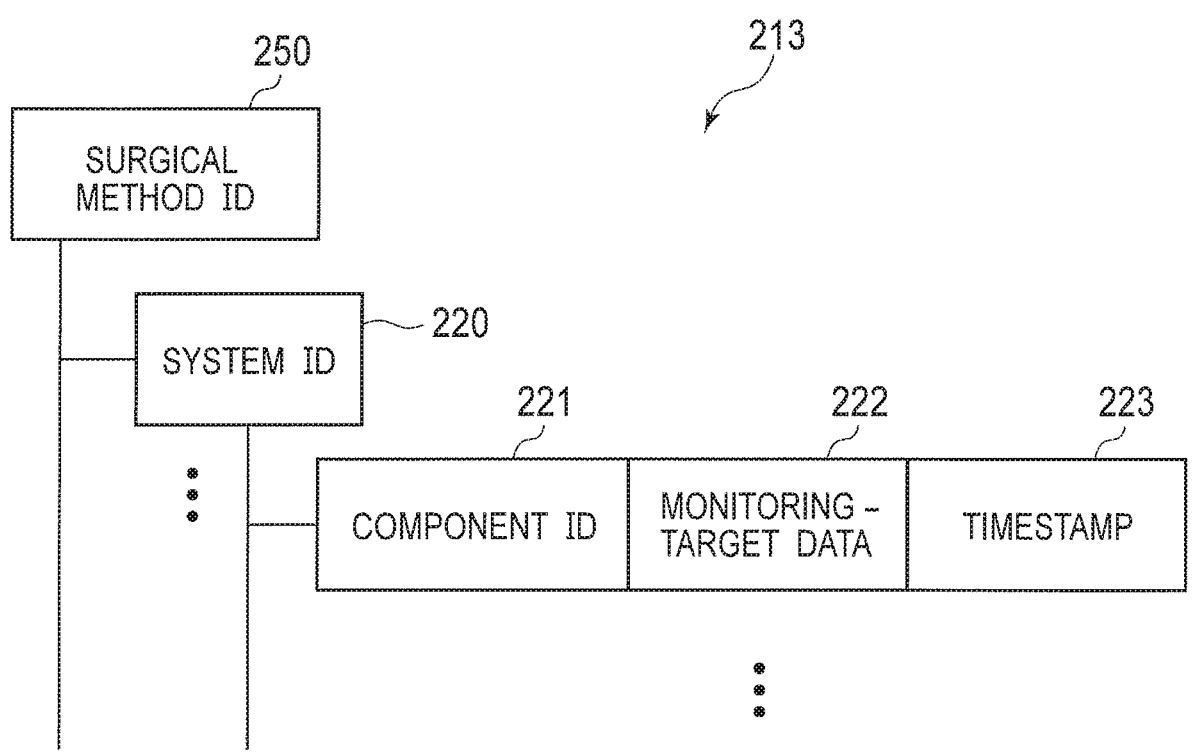
FIG. 19 is a diagram illustrating a data structure in the database according to an embodiment.

FIG. 19 illustrates an example of the data form of database 213. Data management unit 211 of data center 201 stores the data transmitted from each surgery robot (the data exemplarily illustrated in FIG. 15A or FIG. 15B) into database 213 in association with surgical method ID 250 indicating the method of the surgery.

Data management unit 211 stores sets of component ID 221, monitoring-target data 222, and timestamp 223 into database 213 for each system ID 220. Data analysis unit 212 can generate simulation data for a particular surgical method implemented by a surgery robot by arranging, in temporal order, pieces of data being found by using surgical method ID 250 and system ID 220. Data analysis unit 212 may generate simulation data based solely on data on specific motions in a particular surgical method.

The service person at support center 205 can educate customers about how to use their surgery robot by installing simulation data into a surgery robot for educating the customers.

As described above, with above-described system 200, it is possible to remotely provide support for proper operation of the surgery robots via a network based on a robot technician's judgment.

Also, it is possible to collect a large amount of data to data center 201 and, by analyzing this big data, it is possible to analyze the frequency of abnormalities, the tendency of failures, and the like in the surgery robots for combinations of motions. With this analysis, it is possible to find a sign of a future abnormality or failure or the like and thus find a solution in advance.

The amount of information on a medical robot increases if it is collected from medical robots operating in multiple operating rooms. In this way, it is possible to provide more elaborated support for a medical robot.

However, none of Related Art 1 to 3 discloses a technique for collecting information from multiple medical robots.

According to the embodiments described above, more elaborated support can be provided for a medical robot based on information collected from multiple medical robots.

Note that in the above-described embodiment, the description has been given of the case where a service person at support center 205 responds. However, computer 210 of data center 201 can respond by means of program without any service person for preventive solution support and the like. The analysis on the data stored in data center 201 and motion commands may also be other than those responded through support center 205.

Also, in the above-described embodiment, surgery systems 100 including surgery robots have been exemplarily described. The invention is not limited to surgery systems 100 including surgery robots but is applicable to medical robot systems including medical robots in general.

Furthermore, the above-described embodiment merely illustrates one example. Various changes can be made without departing from the spirit of the invention, and the invention is not limited to the above-described embodiment.

The invention claimed is:

1. A medical-robot monitoring method for monitoring remotely located medical robots each including a movable part, the method comprising:

collecting, by a computer at a data center, from each of the medical robots over an external network, data of a measured value of a motion of the movable part of the medical robot;

statistically analyzing, by the computer at the data center, the data collected from the medical robots to calculate, based on the statistically analyzed data, a reference value for determining whether an individual one of the medical robots is normal or abnormal among the medical robots;

comparing, by the computer at the data center, a difference between the reference value and the measured value of one of the medical robots with a threshold, to detect a sign of abnormality of the one of the medical robots in response to determining that the difference exceeds the threshold; and notifying by the computer at the data center, based on the detected sign of abnormality of the one of the medical robots, warning information including the difference from the reference value on the one of the medical robots to a support center or the one of the medical robots.

2. The method of claim 1, wherein the sign of abnormality is detected when the difference exceeds the threshold over a predetermined number of times, which is more than one.

3. The method of claim 1, wherein the sign of abnormality is detected when the difference exceeds the threshold over a predetermined period of time.

4. The method of claim 1, wherein the reference value is regularly updated based on newly collected data.

5. The method of claim 1, further comprising remotely controlling, in response to detecting the sign of abnormality, the one of the medical robots having the sign of abnormality over the network.

6. The method of claim 1, wherein the data collected from the medical robots includes a set of data regarding multiple types of movable parts built in the medical robots.

7. The method of claim 1, wherein the reference value is generated for each type of movable parts built in each of the medical robots.

8. The method of claim 1, wherein the medical robots includes first and second medical robots, the first medical robot is installed at a first facility, the second medical robot is installed at a second facility different from the first facility and the computer at the data center is installed at a third facility different from the first facility and the second facility.

9. The method of claim 1, wherein each of the medical robots includes a master manipulator and a slave robot capable of surgically accessing to a patient, and the data collected from the medical robots includes a motion of the slave robot of each of the medical robots.

10. The method of claim 1, wherein statistically analyzing, by the computer at the data center, the data collected from the medical robots to calculate, based on the statistically analyzed data, a reference value for determining whether an individual one of the medical robots is normal or abnormal among the medical robots comprises calculating a mean and a standard deviation of the data collected from the medical robots, and comparing, by the computer at the data center, a difference between the reference value and the measured value of one of the medical robots with a threshold to detect a sign of abnormality of-the one of the medical robots in response to determining that the difference exceeds the threshold, comprises comparing, by the computer at the data center, a difference between the mean and the measured value of one of the medical robots with the threshold that is calculated based on the standard deviation, to detect a sign of abnormality of the one of the medical robots in response to determining that the difference exceeds the threshold.

11. A medical-robot managing method comprising:
  collecting, by a computer at a data center, from each of remotely located medical robots over an external network, data of a measured value of a motion of a movable part of the medical robot;
  statistically analyzing, by the computer at the data center, the data collected from the medical robots to calculate, based on the statistically analyzed data, a reference value for determining whether an individual one of the medical robots is normal or abnormal among the medical robots;
  comparing a difference between the reference value and the measured value of one of the medical robots with a threshold, to detect a sign of abnormality of the one of the medical robots in response to determining that the difference exceeds the threshold; and
  remotely controlling, in response to detecting the sign of abnormality of the one of the medical robots, the one of the medical robots.

12. The method of claim 11, wherein the reference value is regularly updated based on newly collected data.

13. The method of claim 11, wherein data collected from the medical robots includes a set of data regarding multiple types of movable parts built in the medical robots.

14. The method of claim 11, wherein the reference value is generated for each type of movable parts built in the medical robots.

15. The method of claim 11, wherein the medical robots includes first and second medical robots, the first medical robot is installed at a first facility, the second medical robot is installed at a second facility different from the first facility and a data analysis apparatus is installed at a third facility different from the first facility and second facility.

16. The method of claim 11, wherein the medical robot includes a master manipulator and a slave robot capable of surgically accessing to a patient, and the data collected from the medical robots includes a motion of the slave robot.

17. A medical-robot system comprising:
  medical robots respectively located in different operation rooms, each of the medical robots including a movable part;
  a data analysis computer configured to:
    collect from each of the medical robots over an external network, data of a measured value of a motion of the movable part of the medical robot;
    statistically analyze the data collected from the medical robots to calculate, based on the statistically analyzed data, a reference value for determining whether an individual one of the medical robots is normal or abnormal among the medical robots;
    compare a difference between the reference value and the measured value of one of the medical robots with a threshold, to detect a sign of abnormality of the one of the medical robots in response to determining that the difference exceeds the threshold; and
    notify, based on the detected sign of abnormality of the one of the medical robots, warning information including the difference from the reference value on the one of the medical robots to a support center or the one of the medical robots.

* * * * *